US012018325B2

(12) United States Patent
Ju et al.

(10) Patent No.: US 12,018,325 B2
(45) Date of Patent: Jun. 25, 2024

(54) 3'-O-MODIFIED NUCLEOTIDE ANALOGUES WITH DIFFERENT CLEAVABLE LINKERS FOR ATTACHING FLUORESCENT LABELS TO THE BASE FOR DNA SEQUENCING BY SYNTHESIS

(71) Applicants: Jingyue Ju, Englewood Cliffs, NJ (US); Xiaoxu Li, New York, NY (US); Xin Chen, New York, NY (US); Shiv Kumar, Belle Mead, NJ (US); James Russo, New York, NY (US); Minchen Chien, Tenafly, NJ (US)

(72) Inventors: Jingyue Ju, Englewood Cliffs, NJ (US); Xiaoxu Li, New York, NY (US); Xin Chen, New York, NY (US); Shiv Kumar, Belle Mead, NJ (US); James Russo, New York, NY (US); Minchen Chien, Tenafly, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 419 days.

(21) Appl. No.: 16/498,132

(22) PCT Filed: Mar. 28, 2018

(86) PCT No.: PCT/US2018/024895
§ 371 (c)(1),
(2) Date: Sep. 26, 2019

(87) PCT Pub. No.: WO2018/183538
PCT Pub. Date: Oct. 4, 2018

(65) Prior Publication Data
US 2021/0285041 A1 Sep. 16, 2021

Related U.S. Application Data
(60) Provisional application No. 62/477,947, filed on Mar. 28, 2017.

(51) Int. Cl.
*C12Q 1/68* (2018.01)
*C07H 19/10* (2006.01)
*C07H 19/20* (2006.01)
*C12Q 1/6869* (2018.01)

(52) U.S. Cl.
CPC .......... *C12Q 1/6869* (2013.01); *C07H 19/10* (2013.01); *C07H 19/20* (2013.01)

(58) Field of Classification Search
CPC ....... C12Q 1/6869; C07H 19/10; C07H 19/20
See application file for complete search history.

(56) References Cited

U.S. PATENT DOCUMENTS

| 5,034,036 | A | 7/1991 | Summerton |
| 5,235,033 | A | 8/1993 | Summerton |
| 5,804,386 | A | 9/1998 | Ju |
| 5,814,454 | A | 9/1998 | Ju |
| 5,876,936 | A | 3/1999 | Ju |
| 5,952,180 | A | 9/1999 | Ju |
| 6,046,005 | A | 4/2000 | Ju et al. |
| 6,485,944 | B1 | 11/2002 | Church |
| 6,627,748 | B1 | 9/2003 | Ju et al. |
| 6,664,079 | B2 | 12/2003 | Ju et al. |
| 7,074,597 | B2 | 7/2006 | Ju |
| 7,279,563 | B2 | 10/2007 | Kwiatkowski |
| 7,345,159 | B2 | 3/2008 | Ju et al. |
| 7,414,116 | B2 | 8/2008 | Milton |
| 7,541,444 | B2 | 6/2009 | Milton |
| 7,566,537 | B2 | 7/2009 | Barnes |
| 7,622,279 | B2 | 11/2009 | Ju |
| 7,635,578 | B2 | 12/2009 | Ju et al. |
| 7,713,698 | B2 | 5/2010 | Ju et al. |
| 7,771,973 | B2 | 8/2010 | Milton |
| 7,790,869 | B2 | 9/2010 | Ju et al. |
| 7,883,869 | B2 | 2/2011 | Ju et al. |
| 7,982,029 | B2 | 7/2011 | Ju et al. |
| 8,071,739 | B2 | 12/2011 | Milton |
| 8,088,575 | B2 | 1/2012 | Ju et al. |
| 8,114,973 | B2 | 2/2012 | Siddiqi |
| 8,298,792 | B2 | 10/2012 | Ju et al. |
| 8,399,188 | B2 | 3/2013 | Zhao |
| 8,597,881 | B2 | 12/2013 | Milton |
| 8,796,432 | B2 | 8/2014 | Ju et al. |
| 8,889,348 | B2 | 11/2014 | Ju |
| 8,900,810 | B2 | 12/2014 | Gordon et al. |
| 9,115,163 | B2 | 8/2015 | Ju et al. |
| 9,121,060 | B2 | 9/2015 | Milton |
| 9,121,062 | B2 | 9/2015 | Balasubramanian |
| 9,133,511 | B2 | 9/2015 | Ju et al. |

(Continued)

FOREIGN PATENT DOCUMENTS

| CN | 109476694 A | 3/2019 |
| EP | 2876166 | 5/2015 |

(Continued)

OTHER PUBLICATIONS

International Search Report issued Aug. 9, 2018 in connection with PCT International Application No. PCT/US2018/024895.
Written Opinion of the International Searching Authority issued Aug. 9, 2018 in connection with PCT International Application No. PCT/US2018/024895.
Communication pursuant to Rule 62 EPC issued Apr. 19, 2021 by European Patent Office in connection with counterpart European Application No. 18774642.5.
Turcatti G, Romieu A, Fedurco M, Tairi AP. A new class of cleavable fluorescent nucleotides: synthesis and optimization as reversible terminators for DNA sequencing by synthesis. Nucleic Acids Res. Mar. 2008;36(4):e25. doi: 10.1093/nar/gkn021. Epub Feb. 7, 2008. PMID: 18263613; PMCID: PMC2275100.

(Continued)

*Primary Examiner* — Jezia Riley
(74) *Attorney, Agent, or Firm* — Gary J. Gershik

(57) ABSTRACT

Disclosed herein, inter alia, are nucleotide analogues, and methods of use thereof, having cleavable orthogonal linkers.

20 Claims, 11 Drawing Sheets

(56) References Cited

U.S. PATENT DOCUMENTS

| | | | |
|---|---|---|---|
| 9,169,510 | B2 | 10/2015 | Ju et al. |
| 9,175,342 | B2 | 11/2015 | Ju et al. |
| 9,255,292 | B2 | 2/2016 | Ju et al. |
| 9,297,042 | B2 | 3/2016 | Ju et al. |
| 9,388,464 | B2 | 7/2016 | Milton |
| 9,410,200 | B2 | 8/2016 | Balasubramanian |
| 9,453,258 | B2 | 9/2016 | Kain |
| 9,528,151 | B2 | 12/2016 | Ju et al. |
| 9,593,373 | B2 | 3/2017 | Liu |
| 9,624,539 | B2 | 4/2017 | Ju et al. |
| 9,670,539 | B2 | 6/2017 | Ju et al. |
| 9,708,358 | B2 | 7/2017 | Ju et al. |
| 9,718,852 | B2 | 8/2017 | Ju et al. |
| 9,719,139 | B2 | 8/2017 | Ju et al. |
| 9,725,480 | B2 | 8/2017 | Ju et al. |
| 9,868,985 | B2 | 1/2018 | Ju et al. |
| 9,890,426 | B2 | 2/2018 | Ju et al. |
| 10,000,801 | B2 | 6/2018 | Ju et al. |
| 10,144,961 | B2 | 12/2018 | Ju et al. |
| 10,190,157 | B2 | 1/2019 | Wu |
| 10,240,195 | B2 | 3/2019 | Fuller et al. |
| 10,246,479 | B2 | 4/2019 | Ju et al. |
| 10,260,094 | B2 | 4/2019 | Ju et al. |
| 10,273,539 | B2 | 4/2019 | Marma et al. |
| 10,301,346 | B2 | 5/2019 | Marma |
| 10,336,785 | B2 | 7/2019 | Marma et al. |
| 11,085,076 | B2 | 8/2021 | Ju |
| 11,089,353 | B1 | 8/2021 | Morris |
| 11,266,673 | B2 | 3/2022 | Ju |
| 2002/0015961 | A1 | 2/2002 | Kwiatkowski |
| 2003/0027140 | A1 | 2/2003 | Ju et al. |
| 2006/0003383 | A1 | 1/2006 | Graham |
| 2006/0057565 | A1 | 3/2006 | Ju et al. |
| 2006/0188901 | A1 | 8/2006 | Barnes et al. |
| 2006/0252038 | A1 | 11/2006 | Ju |
| 2007/0009980 | A1 | 1/2007 | Graham |
| 2007/0219367 | A1 | 9/2007 | Shchepinov |
| 2009/0047699 | A1 | 2/2009 | Graham |
| 2011/0014611 | A1 | 1/2011 | Ju |
| 2012/0142006 | A1 | 6/2012 | Ju et al. |
| 2012/0156671 | A1 | 6/2012 | Liu |
| 2012/0156680 | A1 | 6/2012 | Ju et al. |
| 2012/0329042 | A1 | 12/2012 | Beechem et al. |
| 2013/0264207 | A1 | 10/2013 | Ju et al. |
| 2013/0280700 | A1 | 10/2013 | Ju et al. |
| 2015/0037788 | A1 | 2/2015 | Ju |
| 2015/0080232 | A1 | 3/2015 | Ju |
| 2015/0140561 | A1 | 5/2015 | Bergmann et al. |
| 2015/0197800 | A1 | 7/2015 | Ju et al. |
| 2015/0232928 | A1 | 8/2015 | Fu et al. |
| 2015/0368710 | A1 | 12/2015 | Fuller |
| 2016/0002721 | A1 | 1/2016 | Liu |
| 2016/0024570 | A1 | 1/2016 | Ju et al. |
| 2016/0024574 | A1 | 1/2016 | Ju et al. |
| 2016/0041179 | A1 | 2/2016 | Ju et al. |
| 2016/0108382 | A1 | 4/2016 | Efcavitch |
| 2016/0208313 | A1 | 7/2016 | Ju et al. |
| 2016/0264612 | A1 | 9/2016 | Ju et al. |
| 2016/0265048 | A1 | 9/2016 | Ju et al. |
| 2016/0355541 | A1 | 12/2016 | Jain |
| 2016/0369336 | A1 | 12/2016 | Stupi |
| 2017/0002407 | A1 | 1/2017 | Balasubramanian et al. |
| 2017/0058335 | A1 | 3/2017 | Tao et al. |
| 2017/0137869 | A1 | 5/2017 | Marma et al. |
| 2017/0166961 | A1 | 6/2017 | Liu |
| 2017/0211134 | A1 | 7/2017 | Marma et al. |
| 2017/0283451 | A1 | 10/2017 | Ju et al. |
| 2018/0073071 | A1 | 3/2018 | Ju et al. |
| 2018/0112257 | A1 | 4/2018 | Ju et al. |
| 2018/0201642 | A1 | 7/2018 | Ju et al. |
| 2018/0208774 | A1 | 7/2018 | Marma et al. |
| 2018/0274024 | A1* | 9/2018 | Ju ............... C07H 19/14 |
| 2018/0274025 | A1 | 9/2018 | Marma et al. |
| 2018/0327828 | A1 | 11/2018 | Ju et al. |
| 2019/0031704 | A1 | 1/2019 | Ju et al. |
| 2019/0031705 | A1 | 1/2019 | Ju et al. |
| 2019/0031706 | A1 | 1/2019 | Ju et al. |
| 2019/0085014 | A1 | 3/2019 | Ju et al. |
| 2019/0085015 | A1 | 3/2019 | Ju et al. |
| 2019/0085016 | A1 | 3/2019 | Ju et al. |
| 2019/0085388 | A1 | 3/2019 | Ju et al. |
| 2019/0092805 | A1 | 3/2019 | Ju et al. |
| 2019/0092806 | A1 | 3/2019 | Ju et al. |
| 2019/0112650 | A1 | 4/2019 | Ju et al. |
| 2019/0135850 | A1 | 5/2019 | Ju et al. |
| 2019/0135851 | A1 | 5/2019 | Ju et al. |
| 2019/0136308 | A1 | 5/2019 | Ju et al. |
| 2019/0153527 | A1 | 5/2019 | Ju et al. |
| 2021/0381043 | A1 | 12/2021 | Ju |

FOREIGN PATENT DOCUMENTS

| | | |
|---|---|---|
| EP | 3091026 | 11/2016 |
| EP | 3356381 A4 | 8/2018 |
| EP | 3356381 A4 | 5/2019 |
| WO | WO 2002/022883 | 3/2002 |
| WO | WO 2002/029003 | 4/2002 |
| WO | WO 03/048387 | 6/2003 |
| WO | WO 2008/037568 A2 | 3/2008 |
| WO | WO 2008/144315 A1 | 11/2008 |
| WO | WO 2009/054922 | 4/2009 |
| WO | WO 2012/083249 | 6/2012 |
| WO | WO 2012/162429 | 11/2012 |
| WO | WO 2013/154999 | 10/2013 |
| WO | WO 2013/191793 | 12/2013 |
| WO | WO 2014/144883 | 9/2014 |
| WO | WO 2014/144898 | 9/2014 |
| WO | WO 2015/123430 | 8/2015 |
| WO | WO 2015/148402 | 10/2015 |
| WO | WO 2016/063059 A1 | 4/2016 |
| WO | WO 2016/144973 | 9/2016 |
| WO | WO 2016/154215 | 9/2016 |
| WO | WO 2017/058953 A1 | 4/2017 |
| WO | WO 2017/079498 | 5/2017 |
| WO | WO 2017/087887 | 5/2017 |
| WO | WO 2017/176677 | 10/2017 |
| WO | WO 2017/176679 | 10/2017 |
| WO | WO 2017/205336 | 11/2017 |

OTHER PUBLICATIONS

Response to Communication pursuant to Rule 62 EPC is-sued Apr. 19, 2021 by European Patent Office in connection with counterpart European Application No. 18774642.5.

Office Action issued Jan. 10, 2023 by Chinese Patent Office in connection with counterpart Chinese Application No. 201880035369. 2, including an English summary thereof.

Response filed in response to Jan. 10, 2023 Office Action issued in counterpart Chinese Application No. 2018800353692.

2Second Office Action issued in connection with counterpart Chinese Application No. 2018800353692 and English translation thereof.

Bentley, D.R. et al. (Nov. 6, 2008). "Accurate whole human genome sequencing using reversible terminator chemistry," Nature 456(7218):53-59.

Bergen, K. et al. (Jun. 17, 2013, e-published Jun. 3, 2013). "Structures of KOD and 9°N DNA polymerases complexed with primer template duplex," Chembiochem 14(9):1058-1062.

Bergseid, M. et al. (Nov. 2000). "Small molecule-based chemical affinity system for the purification of proteins," BioTechniques 29(5):1126-1133.

Binauld, S. et al. (Mar. 14, 2013). "Acid-degradable polymers for drug delivery: a decade of innovation," Chem Commun 49(21):2082-2102.

Blackman, M.L. et al. (Oct. 15, 2008, e-published Sep. 18, 2008). "The Tetrazine ligation: fast bioconjugation based on inverse-electron-demand Diels-Alder reactivity," J Am Chem Soc 130(41):13518-13519.

Debets, M.F. et al. (Oct. 14, 2013, e-published Aug. 23, 2013). "Bioorthogonal labelling of biomolecules: new functional handles and ligation methods," Org Biomol Chem 11(38):6439-6455.

(56) References Cited

OTHER PUBLICATIONS

Fuller, C.W. et al. (May 10, 2016, e-published Apr. 18, 2016). "Real-time single-molecule electronic DNA sequencing by synthesis using polymer-tagged nucleotides on a nanopore array," PNAS USA 113(19):5233-5238.
Guillier, F. et al. (Jun. 14, 2000). "Linkers and cleavage strategies in solid-phase organic synthesis and combinatorial chemistry," Chem Rev 100(6):2091-2158.
Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," PNAS USA 105(27):9145-9150.
Hutter, D. et al. (Nov. 2010). "Labeled nucleoside triphosphates with reversibly terminating aminoalkoxyl groups," Nucleosides Nucleotides Nucleic Acids 29(11):879-895.
Inoue, T. et al. (Nov. 2015). "Synthesis of trifluoromethyl ethers and difluoro(methylthio)methyl ethers by the reaction of dithiocarbonates with IF5-pyridine-HF," Journal of Fluorine Chemistry 179:48-52.
Jewett, J.C. et al. (Mar. 24, 2010). "Rapid Cu-free click chemistry with readily synthesized biarylazacyclooctynones," J Am Chem Soc 132(11):3688-3690.
Ju, J. et al. (Dec. 26, 2006, e-published Dec. 14, 2006). "Four-color DNA sequencing by synthesis using cleavable fluorescent nucleotide reversible terminators," PNAS USA 103(52):19635-19640.
Kumar, S. et al. (2012, e-published Sep. 21, 2012). "PEG-labeled nucleotides and nanopore detection for single molecule DNA sequencing by synthesis," Sci Rep 2:684.
Leicher, T. et al. (Dec. 25, 1998). "Coexpression of the KCNA3B gene product with Kv1.5 leads to a novel A-type potassium channel," J Biol Chem 273(52):35095-35101.
Leriche, G. et al. (Jul. 2010). "Optimization of the Azobenzene Scaffold for Reductive Cleavage by Dithionite; Development of an Azobenzene Cleavable Linker for Proteomic Applications," Eur J Org Chem 2010(23):4360-4364.
Marcus-Sekura, C.J. et al. (Aug. 1, 1988). "Techniques for using antisense oligodeoxyribonucleotides to study gene expression," Anal Biochem 172(2):289-295.
Needleman, S.B. et al. (Mar. 1970). "A general method applicable to the search for similarities in the amino acid sequence of two proteins," J Mol Biol 48(3):443-453.
Pearson, W.R. et al. (Apr. 1988). "Improved tools for biological sequence comparison," PNAS USA 85(8):2444-2448.
Rathod, K.M. et al. (2013). "Synthesis and Antimicrobial Activity of Azo Compounds Containing m-Cresol Moiety," Chem Sci Trans 2(1):25-28.
Rosenblum, B.B. et al. (Nov. 15, 1997). "New dye-labeled terminators for improved DNA sequencing patterns," Nucleic Acids Res 25(22):4500-4504.
Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," PNAS USA 102(17):5932-5937.
Shenoi, R.A. et al. (Sep. 12, 2012, e-published Aug. 30, 2012). "Branched multifunctional polyether polyketals: variation of ketal group structure enables unprecedented control over polymer degradation in solution and within cells," J Am Chem Soc 134(36):14945-14957.
Smith T.F. et al. (Dec. 1981). "Comparison of biosequences," Adv Appl Math 2(4):482-489.
Southworth, M.W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," PNAS USA 93(11):5281-5285.
Svagera, Z., Hanzlikova, D., Simek, P., and Husek, P. (2012) Study of disulfide reduction and alkyl chloroformate derivatization of plasma sulfur amino acids using gas chromatography-mass spectrometry. Anal. Bioanal. Chem. 402: 2953-2963.
Tang et al. Synthesis and Application of Four Fluorescence Labeled Nucleotides Through Disulfide as Reversible Terminators in DNA Sequencing by Synthesis. Chem. J. Chinese U. Nov. 2014; 35(11):2346-52, including an English language abstract.
Uhlmann, E. et al. (Jun. 1990). "Antisense oligonucleotides: a new therapeutic principle," Chemical Reviews 90(4):543-584.
Weintraub, H.M. (Jan. 1990). "Antisense RNA and DNA," Sci Am 262(1):40-46.
Wolfram Schumacher, Christof Holliger, Alexander J.B Zehnder, Wilfred R Hagen, Redox chemistry of cobalamin and iron-sulfur cofactors in the tetrachloroethene reductase of Dehalobacter restrictus, FEBS Letters, vol. 409, Issue 3, 1997, pp. 421-425, ISSN 0014-5793.
Wu, J. et al. (Oct. 16, 2007, e-published Oct. 8, 2007). "3'-O-modified nucleotides as reversible terminators for pyrosequencing," PNAS USA 104(42):16462-16467; and.
Zhu, Z. et al. (Aug. 25, 1994). "Directly labeled DNA probes using fluorescent nucleotides with different length linkers," Nucleic Acids Res 22(16):3418-3422.
Qiu C, Kumar S, Guo J, Yu L, Guo W, Shi S, Russo JJ, Ju J. Design and synthesis of cleavable biotinylated dideoxynucleotides for DNA sequencing by matrix-assisted laser desorption/ionization time-of-flight mass spectrometry. Anal Biochem. Aug. 1, 20125;427(2):193-201. doi: 10.1016/j.ab.2012.04.021. Epub Apr. 25, 2012. PMID: 22543091.

* cited by examiner

3'-O-MODIFIED NUCLEOTIDE ANALOGUES WITH DIFFERENT CLEAVABLE LINKERS FOR ATTACHING FLUORESCENT LABELS TO THE BASE FOR DNA SEQUENCING BY SYNTHESIS

CROSS-REFERENCE TO RELATED APPLICATIONS

This application is a § 371 national stage of PCT International Application No. PCT/US2018/024895, filed Mar. 28, 2018, and claims the benefit of U.S. Provisional Application No. 62/477,947, filed Mar. 28, 2017, the contents of each of which are hereby incorporated by reference.

Throughout this application, various publications and patents are referenced. Full citations for these references may be found at the end of the specification immediately preceding the claims. The disclosures of these publications and patents in their entirety are hereby incorporated by reference into this application to more fully describe the state of the art to which this invention pertains.

BACKGROUND OF THE INVENTION

DNA sequencing is a fundamental tool in biological and medical research, and is especially important for the paradigm of personalized medicine. Various new DNA sequencing methods have been investigated with the aim of eventually realizing the goal of the $1,000 genome; the dominant method is sequencing by synthesis (SBS), an approach that determines DNA sequences during the polymerase reaction (Hyman 1988; Ronaghi et al. 1998; Ju et al. 2003; Li 2003; Braslavsky et al. 2003; Ruparel et al. 2005; Margulies et al. 2005; Ju et al. 2006; Wu et al. 2007; Guo et al. 2008; Bentley et al. 2008; Harris et al. 2008; Eid et al. 2009; Rothberg et al. 2011). The currently widely used high-throughput SBS technology (Bentley et al. 2008) uses cleavable fluorescent nucleotide reversible terminator (NRT) sequencing chemistry developed previously (Ju et al. 2003; Ju et al. 2006). These cleavable fluorescent NRTs were designed based on the following rationale: each of the four nucleotides (A, C, G, T) is modified by attaching a unique cleavable fluorophore to the specific location of the base and capping the 3'-OH group with a small reversible moiety so that they are still recognized by DNA polymerase as substrates. Thus, the cleavable fluorescent NRTs involve two site modifications (Ju et al. 2003; Ju et al. 2006): a fluorescent dye to serve as a reporter group on the base and a small chemical moiety to cap the 3'-OH group to temporarily terminate the polymerase reaction after nucleotide incorporation for sequence determination. After incorporation and signal detection, the fluorophore is cleaved and the 3'-OH capping moiety removed to resume the polymerase reaction in the next cycle. These cleavable fluorescent NRTs have proved to be good substrates for reengineered polymerases and have been used extensively in next generation DNA sequencing systems (Ju et al. 2006; Bentley et al. 2008). Moreover, they enable accurate determination of homopolymer sequences, since only one base is identified in each cycle.

An SBS approach using cleavable fluorescent nucleotide analogues as reversible terminators to sequence surface-immobilized DNA has been used (Ju et al. 2003; Li et al. 2003; Ruparel et al. 2005; Ju et al. 2006; Wu et al. 2007; Guo et al. 2008). In this approach, the nucleotides are modified at two specific locations so that they are still recognized by DNA polymerase as substrates: (i) a different fluorophore with a distinct fluorescent emission is linked to the specific location of each of the four bases through a cleavable linker and (ii) the 3'-OH group is capped by a small chemically reversible moiety. DNA polymerase incorporates only a single nucleotide analogue complementary to the base on a DNA template covalently linked to a surface. After incorporation, the unique fluorescence emission is detected to identify the incorporated nucleotide. The fluorophore is subsequently removed and 3'-OH group is chemically regenerated, which allows the next cycle of the polymerase reaction to proceed. Because the large surface on a DNA chip can have a high density of different DNA templates spotted, each cycle can identify many bases in parallel, allowing the simultaneous sequencing of a large number of DNA molecules. Previous research efforts have firmly established the molecular level strategy to rationally modify the nucleotides by attaching a cleavable fluorescent dye to the base and reversibly capping the 3'-OH with a small moiety for SBS.

A class of nucleotide analogues with unprotected 3'-OH and a cleavable disulfide linker attached between the base and fluorescent dye has been reported (Turcatti et al. 2008; Mitra et al. 2003). However, after DNA polymerase catalyzed extension reaction on the primer/template and imaging the incorporated base, the cleavage of the disulfide linkage generates a free reactive —SH group which has to be capped with alkylating agent, iodoacetamide as shown below, before the second extension reaction can be carried out. This capping step not only adds an extra step in the process but also limits the addition of multiple nucleotides in a row because of the long remnant tail on the nucleotide base moiety. With this approach the sequencing read length is limited to only 10 bases (Turcatti et al. 2008). Other disulfide based approaches require a similar capping reaction to render the free SH group unreactive (Mitra et al. 2003).

For the long read SBS strategy it is preferable that the cleavable linker is stable during the sequencing reactions, requires less manipulations and does not leave a long tail on the base after the cleavage reaction.

BRIEF SUMMARY OF THE INVENTION

The present invention provides a nucleotide analogue comprising: (i) a deoxyribose or ribose, (ii) a base attached to the 1' position of the deoxyribose or ribose wherein the base is selected from the group consisting of A, T, C, G, and U or derivatives thereof, (iii) blocking group bound to the 3'-oxygen of the deoxyribose or ribose, and (iv) a detectable label bound to the base via a cleavable linker.

The present invention further provides a composition comprising four different types of nucleotide analogue, wherein each type of nucleotide analogue comprises: a base selected from the group consisting of A, T, C, G, or U or derivatives thereof, (a deoxyribose or ribose, and a blocking group bound to the 3'-oxygen of the deoxyribose or ribose, and (i) the first type of nucleotide analogue comprises a first type of detectable label bound to the base via a first type of linker;
  (ii) the second type of nucleotide analogue comprises a second type of detectable label bound to the base via a second type of linker;
  (iii) the third type of nucleotide analogue comprises the first type of detectable label bound to the base via the second type of linker; and
  (iv) the fourth type of nucleotide analogue comprises the second type of detectable label bound to the base via the first type of linker;

the first type and second type of linker are different, and the first type and second type of detectable label are different.

The subject invention provides a method for determining the nucleotide sequence of a single-stranded nucleic acid comprising:
  a) contacting the single-stranded nucleic acid, with a nucleic acid polymerase and four types of tagged nucleotide analogues under conditions permitting the nucleic acid polymerase to catalyze incorporation of one of the tagged nucleotide analogues into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a nucleic acid extension product, wherein each type of the at least four types of tagged nucleotide analogues comprises: a base which is adenine, guanine, cytosine, thymine, or uracil, or a derivative of each thereof, a deoxyribose or ribose, and a cleavable blocking group bound to the 3'-oxygen of the deoxyribose or ribose that prevents the polymerase from catalyzing the incorporation of a subsequent nucleotide, and
    (i) the first type of nucleotide analogue comprises a first type of base and a first type of detectable label bound to the base via a first type of linker;
    (ii) the second type of nucleotide analogue comprises a second type of base and a second type of detectable label bound to the base via a second type of linker;
    (iii) the third type of nucleotide analogue comprises a third type of base and the first type of detectable label bound to the base via the second type of linker; and
    (iv) the fourth type of nucleotide analogue comprises a fourth type of base and the second type of detectable label bound to the base via the first type of linker;
    wherein the first type and second type of linkers are different, and wherein the first type and second type of detectable label are different;
  b) identifying whether a nucleotide analogue comprising the first type or second type of detectable label was incorporated in step (a);
  c) contacting the incorporated tagged nucleotide analogue with a means of cleaving the first type of linker;
  d) determining whether the label was removed by the means of cleaving in step (c) so as to thereby determine the identity of the incorporated nucleotide analogue;
  e) contacting the incorporated tagged nucleotide analogue with a means of cleaving the second type of linker;
  f) cleaving the 3'-oxygen blocking group so as to thereby form a 3'-OH;
  g) iteratively performing steps (a)-(f) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product,
so as to thereby determine the nucleotide sequence of the single-stranded nucleic acid.

The subject invention provides a method for determining the nucleotide sequence of a single-stranded nucleic acid comprising:
  a) contacting the single-stranded nucleic acid with a nucleic acid polymerase and a first type of tagged nucleotide analogue under conditions permitting the nucleic acid polymerase to catalyze incorporation of the tagged nucleotide analogue into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a DNA extension product,
    wherein the tagged nucleotide analogue comprises a first type of base which is adenine, guanine, cytosine, thymine, or uracil, or a derivative of each thereof, a deoxyribose or ribose, a cleavable blocking group bound to the 3'-oxygen of the deoxyribose or ribose that prevents the polymerase from catalyzing the incorporation of a subsequent nucleotide, and a first type of detectable label bound to the base via a first type of linker,
    and if a tagged nucleotide is not incorporated, iteratively repeating the contacting with a second, third, and fourth type of tagged nucleotide analogue until a tagged nucleotide analogue is incorporated, wherein
    (i) the second type of nucleotide analogue comprises a second type of base and a second type of detectable label bound to the base via a second type of linker;
    (ii) the third type of nucleotide analogue comprises a third type of base and the first type of detectable label bound to the base via the second type of linker; and
    (iii) the fourth type of nucleotide analogue comprises a fourth type of base and the second type of detectable label bound to the base via the first type of linker;
    wherein the first type and second type of linkers are different, and wherein the first type and second type of detectable label are different;
  b) identifying whether a nucleotide analogue comprising the first type or second type of detectable label was incorporated in step (a);
  c) contacting the incorporated nucleotide analogue with a means of cleaving the first type of linker;
  d) determining whether the detectable label was removed by the means of cleaving in step (c) so as to thereby determine the identity of the incorporated nucleotide analogue;
  e) contacting the incorporated tagged nucleotide analogue with a means of cleaving the second type of linker;
  f) cleaving the 3'-oxygen blocking group so as to thereby form a 3'-OH;
  g) iteratively performing steps (a)-(f) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product, so as to thereby determine the nucleotide sequence of the single-stranded nucleic acid.

The invention provides a method for determining the nucleotide sequence of a single-stranded nucleic acid comprising:
  a) contacting the single-stranded nucleic acid, with a nucleic acid polymerase and four types of tagged nucleotide analogues under conditions permitting the nucleic acid polymerase to catalyze incorporation of one of the tagged nucleotide analogues into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a nucleic acid extension product, wherein each type of the at least four types of tagged nucleotide analogues comprises: a base which is adenine, guanine, cytosine, thymine, or uracil, or a derivative of each thereof, a deoxyribose or ribose, and a blocking group bound to the 3'-oxygen of the deoxyribose or ribose that prevents the polymerase from catalyzing the incorporation of a subsequent nucleotide, and (i) the first type of nucleotide analogue comprises a first type of base and a first type of detectable label bound to the base via a first type of linker;

(ii) the second type of nucleotide analogue comprises a second type of base and a second type of detectable label bound to the base via a second type of linker;

(iii) the third type of nucleotide analogue comprises third type of base and the first type of detectable label bound to the base via the second type of linker; and (iv) the fourth type of nucleotide analogue comprises a fourth type of base and the second type of detectable label bound to the base via the first type of linker; and wherein the first type and second type of detectable label are different;

b) contacting the single-stranded nucleic acid with four types of nucleotide reversible terminators, wherein each nucleotide reversible terminator comprises a blocking group to the 3'-oxygen of the deoxyribose or ribose that prevents the polymerase from catalyzing incorporation of a subsequent nucleotide, under conditions permitting the nucleic acid polymerase to catalyze incorporation of one of the nucleotide reversible terminators into the primer if:

(i) the polymerase failed to incorporate a tagged nucleotide analogue in step a), (ii) the nucleotide reversible terminator is complementary to the nucleotide residue of the single-stranded nucleic acid which is immediately 5' to a nucleotide residue of the single-stranded nucleic acid hybridized to the 3' terminal nucleotide residue of the primer, and c) identifying whether a nucleotide analogue comprising the first type or second type of detectable label was incorporated in step (a);

d) contacting the incorporated tagged nucleotide analogue with a means of cleaving the first type of linker;

e) determining whether the label was removed by the means of cleaving in step (c) so as to thereby determine the identity of the incorporated nucleotide analogue;

f) contacting the incorporated tagged nucleotide analogue with a means of cleaving the second type of linker;

g) cleaving the 3'-oxygen blocking group so as to thereby form a 3'-OH;

h) iteratively performing steps (a)-(g) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product, so as to thereby determine the nucleotide sequence of the single-stranded nucleic acid.

The invention provides a method for determining the nucleotide sequence of a single-stranded nucleic acid comprising:

a) contacting the single-stranded nucleic acid with a nucleic acid polymerase and a first type of tagged nucleotide analogue under conditions permitting the nucleic acid polymerase to catalyze incorporation of the tagged nucleotide analogue into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a DNA extension product, wherein the tagged nucleotide analogue comprises a first type of base which is adenine, guanine, cytosine, thymine, or uracil, or a derivative of each thereof, a deoxyribose or ribose, a blocking group bound to the 3'-oxygen of the deoxyribose or ribose that prevents the polymerase from catalyzing the incorporation of a subsequent nucleotide, and a first type of detectable label bound to the base via a first type of linker, and if a tagged nucleotide is not incorporated, iteratively repeating the contacting with a second, third, and fourth type of tagged nucleotide analogue until a tagged nucleotide analogue is incorporated, wherein (i) the second type of nucleotide analogue comprises a second type of base and a second type of detectable label bound to the base via a second type of linker;

(ii) the third type of nucleotide analogue comprises a third type of base and the first type of detectable label bound to the base via the second type of linker; and (iii) the fourth type of nucleotide analogue comprises a fourth type of base and the second type of detectable label bound to the base via the first type of linker;

wherein the first type and second type of linkers are different, and wherein the first type and second type of detectable label are different;

b) contacting the single-stranded nucleic acid with four types of nucleotide reversible terminators wherein each nucleotide reversible terminator comprises a blocking group to the 3'-oxygen of the deoxyribose or ribose that prevents the polymerase from catalyzing incorporation of a subsequent nucleotide, under conditions permitting the nucleic acid polymerase to catalyze incorporation of one of the nucleotide reversible terminators into the primer if:

(i) the polymerase failed to incorporate a tagged nucleotide analogue in step a), and (ii) the nucleotide reversible terminator is complementary to the nucleotide residue of the single-stranded nucleic acid which is immediately 5' to a nucleotide residue of the single-stranded nucleic acid hybridized to the 3' terminal nucleotide residue of the primer;

c) identifying whether a nucleotide analogue comprising the first type or second type of detectable label was incorporated in step (a);

d) contacting the incorporated nucleotide analogue with a means of cleaving the first type of linker;

e) determining whether the detectable label was removed by the means of cleaving in step (c) so as to thereby determine the identity of the incorporated nucleotide analogue;

f) contacting the incorporated tagged nucleotide analogue with a means of cleaving the second type of linker;

g) cleaving the 3'-oxygen blocking group so as to thereby form a 3'-OH.

h) iteratively performing steps (a)-(g) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product, so as to thereby determine the nucleotide sequence of the single-stranded nucleic acid.

The present invention further provides a kit for nucleic acid sequencing, comprising, in separate compartments:

a) Four types of tagged nucleotide analogue, wherein each type of tagged nucleotide analogue comprises a base selected from the group consisting of A, T, C, G, or U or derivatives thereof, a deoxyribose or ribose, and a blocking group bound to the 3'-oxygen of the deoxyribose or ribose, and (i) the first type of nucleotide analogue comprises a first type of base and a first type of detectable label bound to the base via a first type of linker;

(ii) the second type of nucleotide analogue comprises a second type of a base and a second type of detectable label bound to the base via a second type of linker;

(iii) the third type of nucleotide analogue comprises a third type of base and the first type of detectable label bound to the base via the second type of linker; and (iv) the fourth type of nucleotide analogue comprises a fourth type of base and the second type of detectable label bound to the base via the first type of linker;

wherein the first type and second type of linker are different, and the first type and second type of detectable label are different

DETAILED DESCRIPTION OF THE INVENTION

Figure 1A:
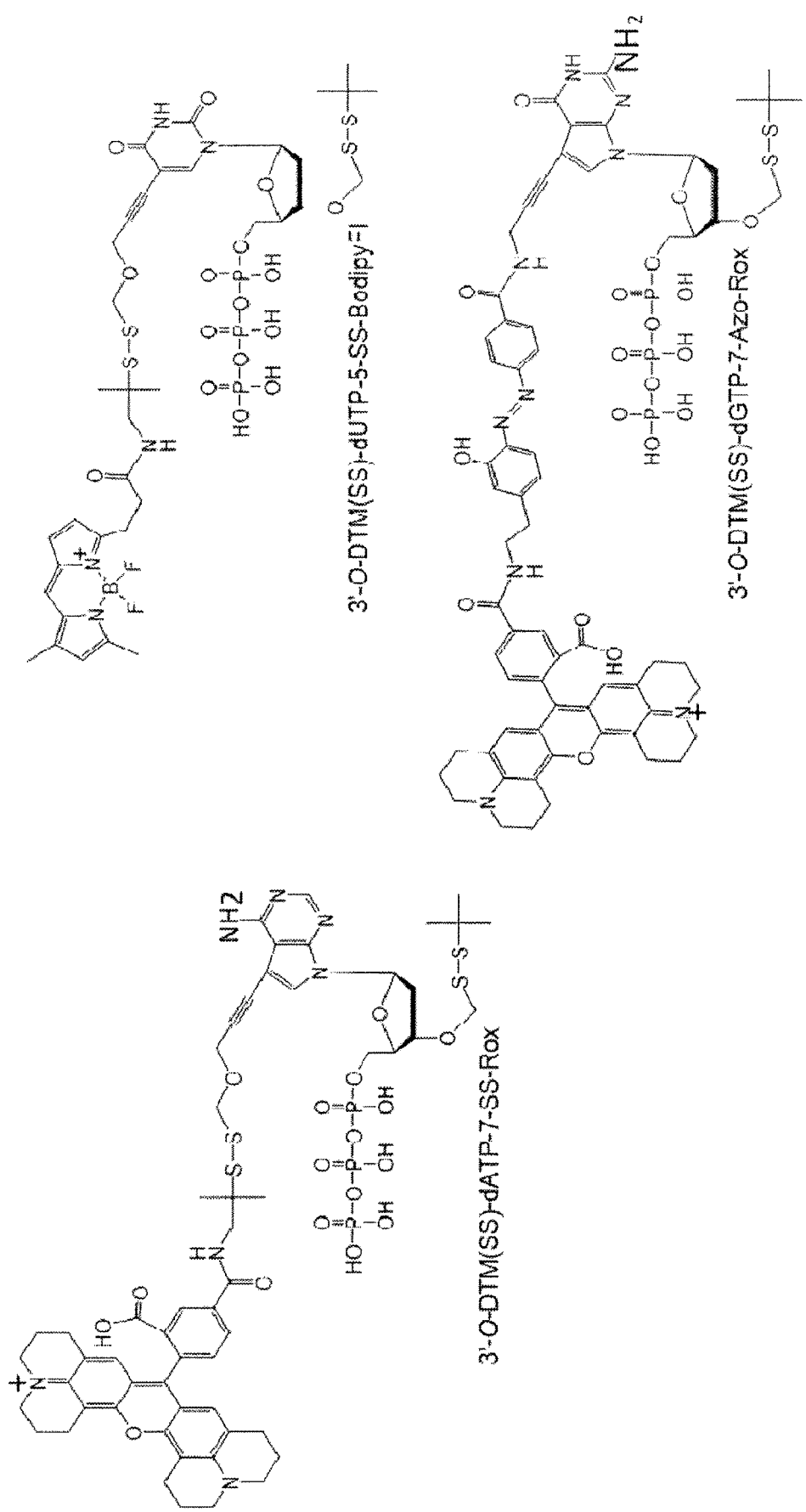
FIG. 1: 3'-O-SS(DTM)-dNTP-SS-Dyes (3'-O-SS-dATP-7-SS-Rox and 3'-O-SS-dUTP-5-SS-BodipyFL) and 3'-O-SS(DTM)-dNTP-SS-Azo-Dyes (3'-O-SS-dGTP-7-Azo-Rox or 3'-O-SS-dGTP-7-SS-Azo-Rox and 3'-O-SS-dCTP-5-Azo-BodipyFL or 3'-O-SS-dCTP-5-SS-Azo-BodipyFL) for 2-color DNA SBS using approach delineated in Scheme 1.

While various embodiments of the invention are shown and described herein, it will be obvious to those skilled in the art that such embodiments are provided by way of example only. Numerous variations, changes, and substitutes may occur without departing from the disclosed invention. It should be understood that various alternatives to the embodiments of the invention described herein may be employed

Terms

As used herein, and unless stated otherwise, each of the following terms shall have the definition set forth below.

A—Adenine;
C—Cytosine;
G—Guanine;
T—Thymine;
U—Uracil;
DNA—Deoxyribonucleic acid;
RNA—Ribonucleic acid;

"Nucleic acid" shall mean, unless otherwise specified, any nucleic acid molecule, including, without limitation, DNA, RNA and hybrids thereof. In an embodiment the nucleic acid bases that form nucleic acid molecules can be the bases A, C, G, T and U, as well as derivatives thereof.

"Derivatives" or "analogues" of these bases are well known in the art, and are exemplified in PCR Systems, Reagents and Consumables (Perkin Elmer Catalogue 1996-1997, Roche Molecular Systems, Inc., Branchburg, New Jersey, USA).

A "nucleotide residue" is a single nucleotide in the state it exists after being incorporated into, and thereby becoming a monomer of, a polynucleotide. Thus, a nucleotide residue is a nucleotide monomer of a polynucleotide, e.g. DNA, which is bound to an adjacent nucleotide monomer of the polynucleotide through a phosphodiester bond at the 3' position of its sugar and is bound to a second adjacent nucleotide monomer through its phosphate group, with the exceptions that (i) a 3' terminal nucleotide residue is only bound to one adjacent nucleotide monomer of the polynucleotide by a phosphodiester bond from its phosphate group, and (ii) a 5' terminal nucleotide residue is only bound to one adjacent nucleotide monomer of the polynucleotide by a phosphodiester bond from the 3' position of its sugar.

"Substrate" or "Surface" shall mean any suitable medium present in the solid phase to which a nucleic acid or an agent may be affixed. Non-limiting examples include chips, beads, nanopore structures and columns. In an embodiment the solid substrate can be present in a solution, including an aqueous solution, a gel, or a fluid.

"Hybridize" shall mean the annealing of one single-stranded nucleic acid to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York). As used herein, hybridization of a primer sequence, or of a DNA extension product, to another nucleic acid shall mean annealing sufficient such that the primer, or DNA extension product, respectively, is extendable by creation of a phosphodiester bond with an available nucleotide or nucleotide analog capable of forming a phosphodiester bond.

As used herein, unless otherwise specified, a base which is "unique" or "different from" another base or a recited list of bases shall mean that the base has a different structure from the other base or bases. For example, a base that is "unique" or "different from" adenine, thymine, and cytosine would include a base that is guanine or a base that is uracil.

As used herein, unless otherwise specified, a label or tag moiety which is "different" from the label or tag moiety of a referenced molecule means that the label or tag moiety has a different chemical structure from the chemical structure of the other/referenced label or tag moiety.

As used herein, unless otherwise specified, "primer" means an oligonucleotide that upon forming a duplex with a polynucleotide template, is capable of acting as a point of polymerase incorporation and extension from its 3' end along the template, thereby resulting in an extended duplex.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" includes groups having 1, 2, . . . , n–1 or n carbons in a linear or branched arrangement. For example, a "C1-C5 alkyl" includes groups having 1, 2, 3, 4, or 5 carbons in a linear or branched arrangement, and specifically includes methyl, ethyl, n-propyl, isopropyl, n-butyl, t-butyl, and pentyl.

As used herein, "alkenyl" refers to a non-aromatic hydrocarbon group, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl group having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon group straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl group having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

Nucleotide analogues that contain a 3'-O-alkyldithiomethyl (3'-O-DTM) blocking group and a fluorophore attached to the base via a DTM or other cleavable linker (Azo, allyl, 2-nitrobenzyl, azidomethyl or dimethyl ketal) are herein disclosed. Two of the nucleotides have the DTM linker on the base and the other two nucleotides have the alternate linker on the base. One of the nucleotides with the DTM linker has Dye1 attached and the other nucleotide with the DTM linker has Dye2 attached. Similarly, one of the nucleotides with the Azo linker has Dye1 attached and the other nucleotide with the Azo linker has Dye 2 attached. Thus, dyes are attached to linkers in an orthogonal fashion. After incorporation of the above set of nucleotides, imaging will be performed to indicate which of two possible nucleotides has been incorporated but not indicate which one specifically. Subsequently, cleavage of the Azo linker and its attached dye and a second round of imaging will determine the exact nucleotide that was incorporated. If the dye is removed, the nucleotide with the Azo linker was incorporated. If the dye remains, the nucleotide with the SS linker on the base was incorporated. Finally, cleavage of the DTM linker will remove any fluorophores remaining on the base as well as restore the 3'-OH group for subsequent cycles of sequencing by synthesis (SBS).

The invention provides for a method of sequencing nucleic acid, comprising: a) extending a priming strand of DNA by incorporating a fluorescently labeled nucleotide into said priming strand; and b) identifying the fluorescently labeled nucleotide, so as to sequence the nucleic acid.

In another embodiment said fluorescently labeled nucleotide has the label linked to the base and a cleavable blocking group on the 3'-hydroxyl group.

In another embodiment, the label is attached to the base via a cleavable linker.

In another embodiment, the 3' OH blocking group is attached to the deoxyribose via a cleavable linker. In another embodiment, the cleavable linker comprises orthogonal chemically cleavable linkers.

In another embodiment, the orthogonal chemically cleavable linker comprises dithiomethyl SS(DTM), Azo, allyl, 2-nitrobenzyl, and dimethyl ketal. In another embodiment, the 3' OH blocking group comprises SS(DTM), azidomethyl, Azo, allyl and 2-nitrobenzyl.

In another embodiment, the nucleotide analogue comprises a deazapurine base.

The subject invention further provides a method of sequencing nucleic acid comprising: a) providing a nucleic acid template hybridized to a primer; b) extending the primer hybridized to said nucleic acid template with a fluorescently labeled nucleotide or nucleotide analogue, wherein said fluorescently labeled nucleotide or nucleotide analogue has the label linked to the base and a blocking group on the 3'-hydroxyl group; and c) identifying the fluorescently labeled nucleotide, so as to sequence the nucleic acid.

In another embodiment said fluorescently labeled nucleotide or nucleotide analogue has the label on the base and a blocking group on the 3'-hydroxyl group. In another embodiment the label is attached to the base via a cleavable linker.

In another embodiment, the nucleotide analogue comprises a deazapurine base.

In another embodiment, the label is attached to the base via a cleavable linker. In another embodiment, the 3' OH blocking group is attached to the deoxyribose via a cleavable linker. In another embodiment, the cleavable linker comprises orthogonal chemically cleavable linkers. In another embodiment, the orthogonal chemically cleavable linker comprises dithiomethyl SS(DTM), Azo, allyl and 2-nitrobenzyl. In another embodiment, the 3' OH blocking group comprises SS(DTM), azidomethyl, Azo, allyl, 2-nitrobenzyl, and dimethyl ketal.

The present invention further provides a method of simultaneously sequencing a plurality of different nucleic acids, comprising: a) extending a plurality of priming DNA strands hybridized to template DNAs, each of which comprises one of said priming DNA strands, by incorporating a fluorescently labeled nucleotide; and b) identifying each fluorescently labeled nucleotide, so as to simultaneously sequence the plurality of different nucleic acids.

In another embodiment, said fluorescently labeled nucleotide or nucleotide analogue has the label on the base and a blocking group on the 3'-hydroxyl group.

In another embodiment, the label is attached to the base via a cleavable linker. In another embodiment, the nucleotide analogue comprises a deazapurine base. In another embodiment, label is attached to the base via a cleavable linker. In another embodiment, the 3' OH blocking group is attached to the deoxyribose via a cleavable linker. In another embodiment, the cleavable linker comprises orthogonal chemically cleavable linkers. In another embodiment, orthogonal chemically cleavable linker comprises dithiomethyl SS(DTM), Azo, allyl, 2-nitrobenzyl, and dimethyl ketal. In another embodiment, the 3' OH blocking group comprises SS(DTM), azidomethyl, Azo, allyl and 2-nitrobenzyl.

In another embodiment, the nucleotide analogue comprises a deazapurine base.

The present invention provides a nucleotide analogue comprising: (i) a deoxyribose or ribose, (ii) a base attached to the 1' position of the deoxyribose or ribose wherein the base is selected from the group consisting of A, T, C, G, and U or derivatives thereof, (iii) blocking group bound to the 3'-oxygen of the deoxyribose or ribose, and (iv) a detectable label bound to the base via a cleavable linker.

In another embodiment, the blocking group is attached to the ribose or deoxyribose via a cleavable linker. In another embodiment, the cleavable linker attached to the blocking group comprises orthogonal chemically cleavable linkers. In another embodiment, the blocking group comprises a dithiomethyl, azidomethyl, azo, allyl, and/or 2-nitrobenzl. In another embodiment, the blocking group comprises an alkyldithiomethyl. In another embodiment, the base is a deazapurine base.

In another embodiment, the cleavable linker attached to the base comprises orthogonal chemically cleavable linkers. In another embodiment, the cleavable linker attached to the base is an alkyldithiomethyl linker an azo linker, an allyl linker, a nitrobenzyl linker, an azidomethyl linker, and/or a dimethyl ketal linker. In another embodiment, detectable label is one or more of a dye, a fluorophore, a fluorescence energy transfer tag, a chemiluminescent compound, a chromophore, a mass tag, an electrophore, a mononucleotide, an oligonucleotide, or a combination thereof. In another embodiment, the detectable label is a fluorophore. In another embodiment, the detectable label is BodipyFL, R6G, ROX, Cy5, or Alexa488. In another embodiment, the nucleotide analogue is 3'-O-SS-dATP-7-SS-Rox, 3'-O-SS-dTTP-5-SS-BodipyFL, 3'-O-SS-dGTP-7-Azo-Rox or 3'-O-SS-dCTP-5-Azo-BodipyFL.

In another embodiment, the cleavable linker is an alkyldithiomethyl linker. In another embodiment, the nucleotide analogue has the structure:

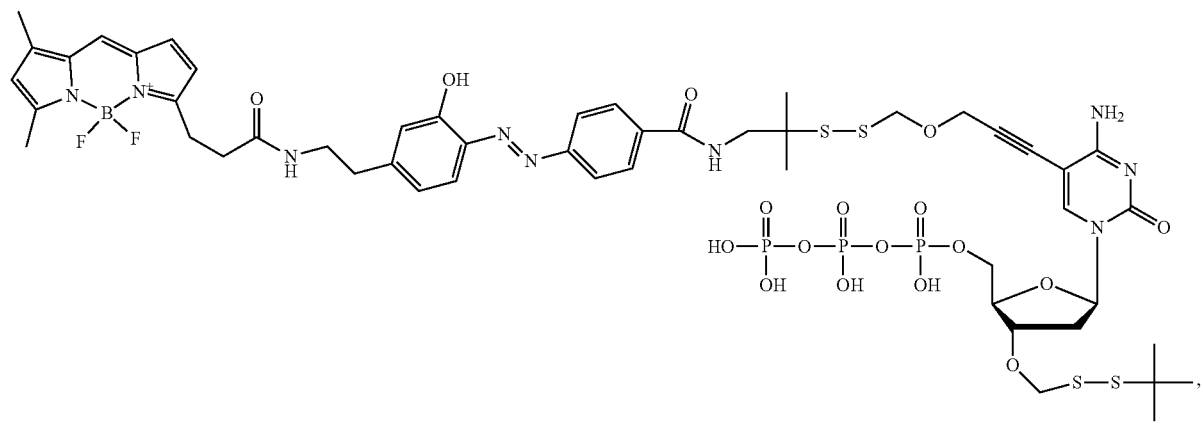
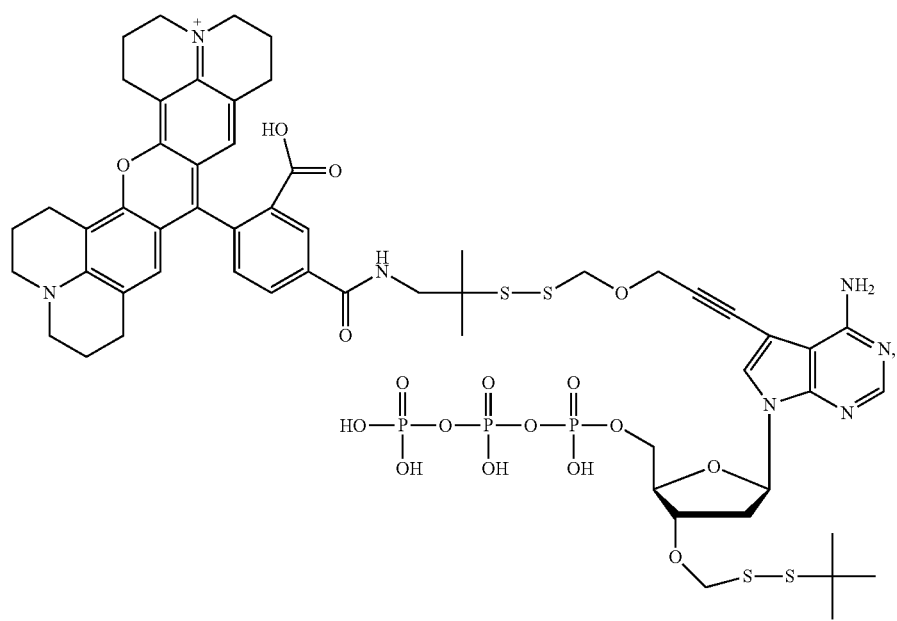
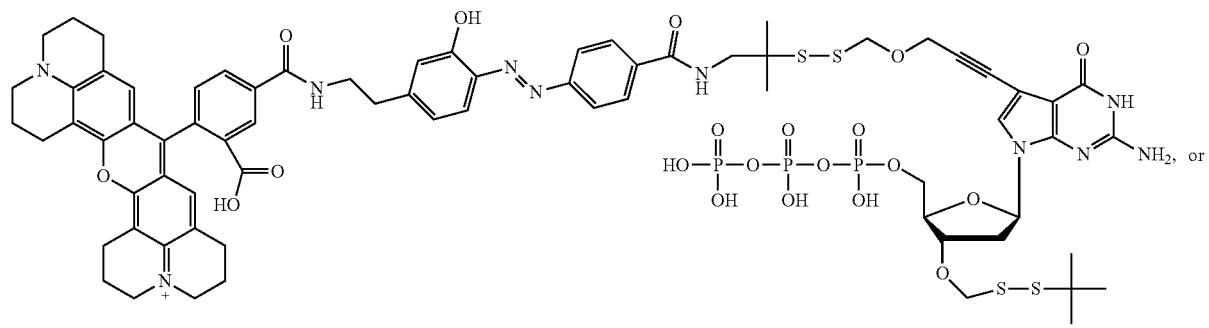

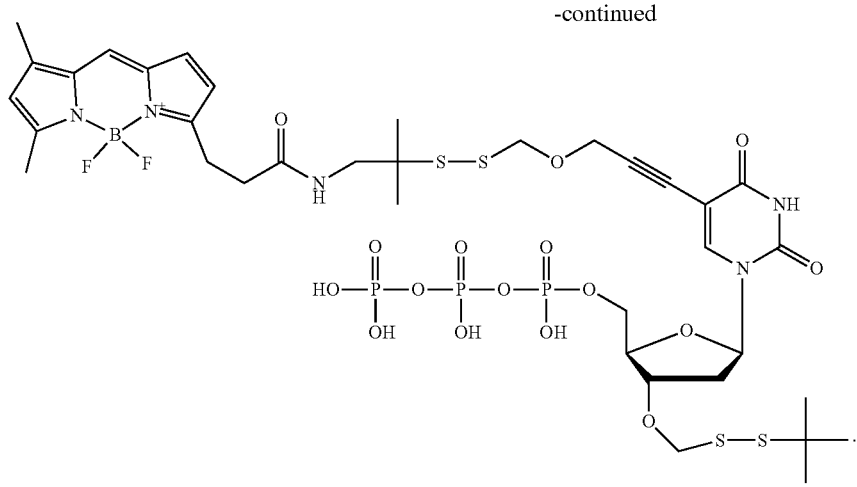
In another embodiment, the cleavable linker is an azo linker. In another embodiment, the nucleotide analogue has the structure:
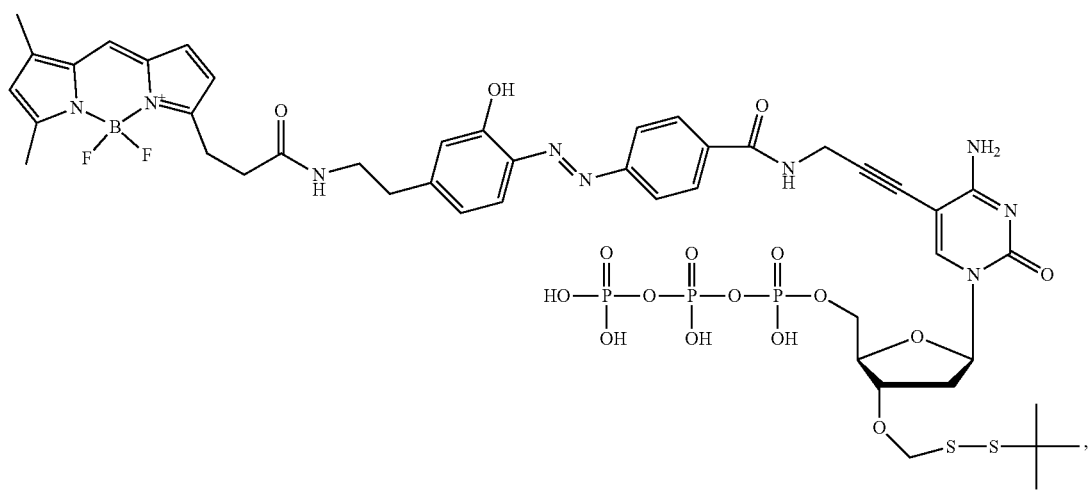
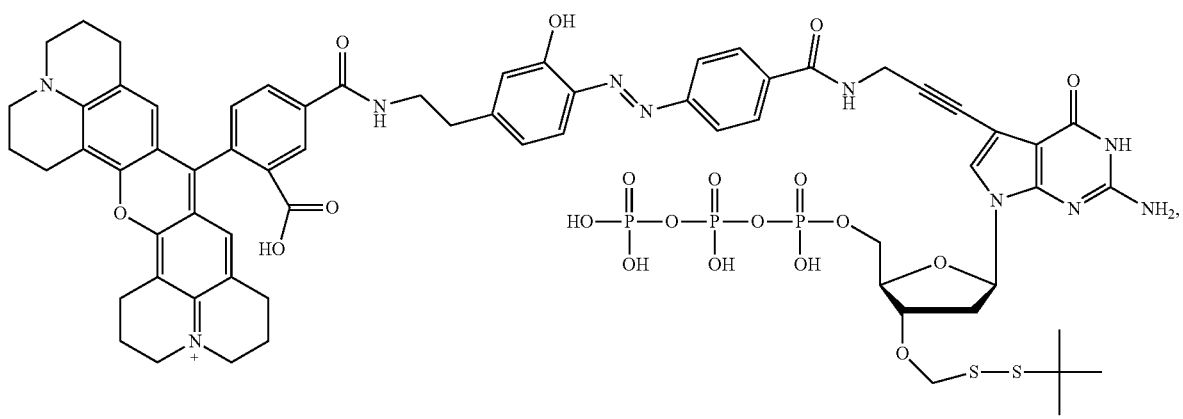

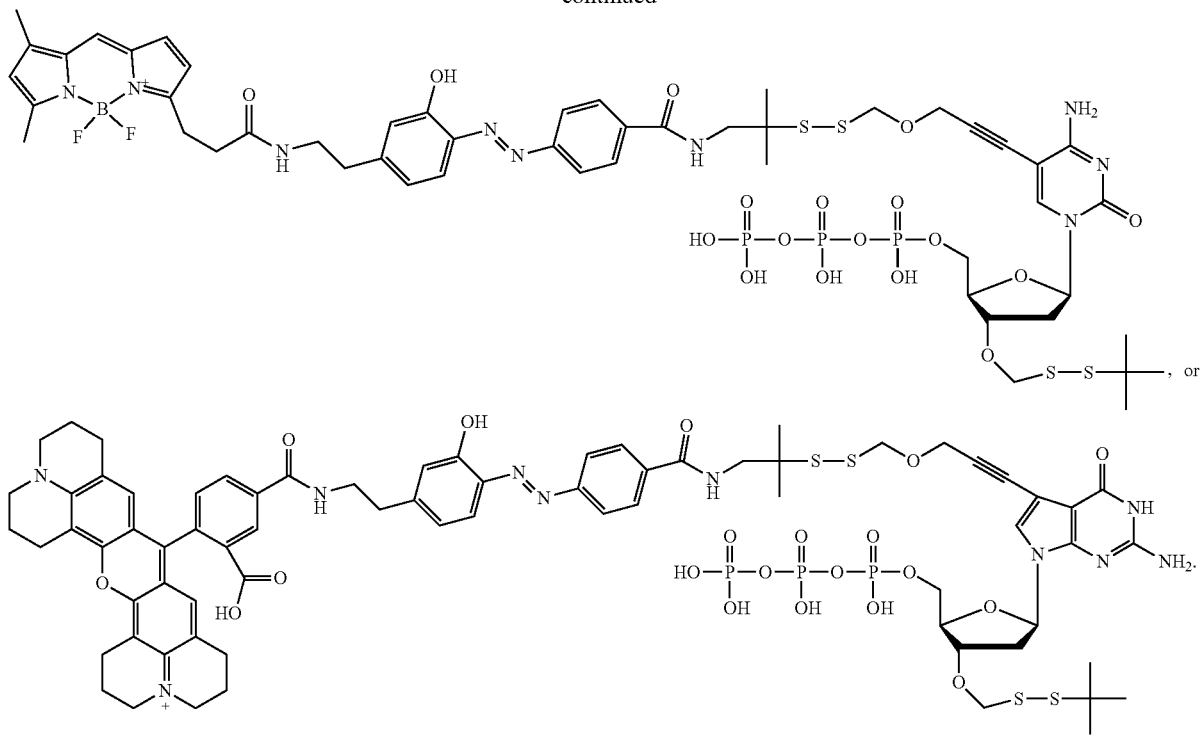

The present invention further provides a composition comprising four different types of nucleotide analogue, wherein each type of nucleotide analogue comprises: a base selected from the group consisting of A, T, C, G, or U or derivatives thereof, (a deoxyribose or ribose, and a blocking group bound to the 3'-oxygen of the deoxyribose or ribose, and
- (i) the first type of nucleotide analogue comprises a first type of detectable label bound to the base via a first type of linker;
- (ii) the second type of nucleotide analogue comprises a second type of detectable label bound to the base via a second type of linker;
- (iii) the third type of nucleotide analogue comprises the first type of detectable label bound to the base via the second type of linker; and
- (iv) the fourth type of nucleotide analogue comprises the second type of detectable label bound to the base via the first type of linker;
the first type and second type of linker are different, and the first type and second type of detectable label are different.

In another embodiment, the blocking group is attached to the ribose or deoxyribose via a cleavable linker. In another embodiment, the cleavable linker attached to the blocking group comprises orthogonal chemically cleavable linkers. In another embodiment, the blocking group comprises a dithiomethyl, azidomethyl, azo, allyl, and/or 2-nitrobenzl. In another embodiment, the blocking group comprises an alkyldithiomethyl.

In another embodiment, the base of one or more of the first, second, third, and/or fourth type of nucleotide analogue comprise a deazapurine base. In another embodiment the first base is A, or derivative thereof and:
- (i) the second base is T/U or a derivative thereof, the third base is C or a derivative thereof, and the fourth base is G or a derivative thereof,
- (ii) the second base is T/U or a derivative thereof, the third base is G or a derivative thereof, and the fourth base is C or a derivative thereof,
- (iii) the second base is C or a derivative thereof, the third base is T/U or a derivative thereof, and the fourth base is G or a derivative thereof,
- (iv) the second base is C or a derivative thereof, the third base is G or a derivative thereof, and the fourth base is T/U or a derivative thereof,
- (v) the second base is G or a derivative thereof, the third base is T/U or a derivative thereof, and the fourth base is C or a derivative thereof, or
- (vi) the second base is G or a derivative thereof, the third base is C or a derivative thereof, and the fourth base is T/U or a derivative thereof.

In another embodiment the first base is T/U, or derivative thereof and:
- (i) the second base is C or a derivative thereof, the third base is A or a derivative thereof, and the fourth base is G or a derivative thereof,
- (ii) the second base is C or a derivative thereof, the third base is G or a derivative thereof, and the fourth base is A or a derivative thereof,
- (iii) the second base is A or a derivative thereof, the third base is C or a derivative thereof, and the fourth base is G or a derivative thereof,
- (iv) the second base is A or a derivative thereof, the third base is G or a derivative thereof, and the fourth base is C or a derivative thereof,
- (v) the second base is G or a derivative thereof, the third base is C or a derivative thereof, and the fourth base is A or a derivative thereof, or
- (vi) the second base is G or a derivative thereof, the third base is A or a derivative thereof, and the fourth base is C or a derivative thereof.

In another embodiment, the first base is C, or derivative thereof and:
(i) the second base is A or a derivative thereof, the third base is T/U or a derivative thereof, and the fourth base is G or a derivative thereof,
(ii) the second base is A or a derivative thereof, the third base is G or a derivative thereof, and the fourth base is T/U or a derivative thereof,
(iii) the second base is T/U or a derivative thereof, the third base is A or a derivative thereof, and the fourth base is G or a derivative thereof,
(iv) the second base is T/U or a derivative thereof, the third base is G or a derivative thereof, and the fourth base is A or a derivative thereof,
(v) the second base is G or a derivative thereof, the third base is T/U or a derivative thereof, and the fourth base is A or a derivative thereof, or
(vi) the second base is G or a derivative thereof, the third base is A or a derivative thereof, and the fourth base is T/U or a derivative thereof.

In another embodiment first base is G, or derivative thereof and:
(i) the second base is C or a derivative thereof, the third base is T/U or a derivative thereof, and the fourth base is A or a derivative thereof,
(ii) the second base is C or a derivative thereof, the third base is A or a derivative thereof, and the fourth base is T/U or a derivative thereof,
(iii) the second base is T/U or a derivative thereof, the third base is A or a derivative thereof, and the fourth base is C or a derivative thereof,
(iv) the second base is T/U or a derivative thereof, the third base is C or a derivative thereof, and the fourth base is A or a derivative thereof,
(v) the second base is A or a derivative thereof, the third base is T/U or a derivative thereof, and the fourth base is C or a derivative thereof, or
(vi) the second base is A or a derivative thereof, the third base is C or a derivative thereof, and the fourth base is T/U or a derivative thereof.

In another embodiment, the first type of linker and/or second type of linker comprises orthogonal chemically cleavable linkers.

In another embodiment, the first and/or second type of linkers comprise one or more of an alkyldithiomethyl linker, an azo linker, an allyl linker, a nitrobenzyl linker, an azidomethyl linker, and/or a dimethyl ketal linker. In another embodiment, the first and/or second type of linkers are chemically cleavable or photocleavable. In another embodiment, first and/or second type of linker are cleavable by a water soluble phosphine, thereby resulting in a 3'-OH. In another embodiment, the water soluble phosphine is tris-(2-carboxyethyl)phosphine (TCEP) or tris(hydroxypropyl)phosphine (THP). In another embodiment, first and/or second type of linkers can be cleaved by sodium dithionite.

In another embodiment, the first and/or second type of detectable label is one or more of a dye, a fluorophore, a fluorescence energy transfer tag, a chemiluminescent compound, a chromophore, a mass tag, an electrophore, a mononucleotide, an oligonucleotide, or a combination thereof. In another embodiment, the first and/or second type of detectable label is a fluorophore. In another embodiment, the first and/or second type of detectable label is BodipyFL, R6G, ROX, Cy5, or Alexa488.

In another embodiment, the composition comprises one or more of 3'-O-SS-dATP-7-SS-Rox, 3'-O-SS-dTTP-5-SS-BodipyFL, 3'-O-SS-dGTP-7-Azo-Rox or 3'-O-SS-dCTP-5-Azo-BodipyFL.

In another embodiment, the first type of linker is an alkyldithiomethyl linker and the second type of linker is an azo linker. In another embodiment, the nucleotide analogues are selected from the group comprising:

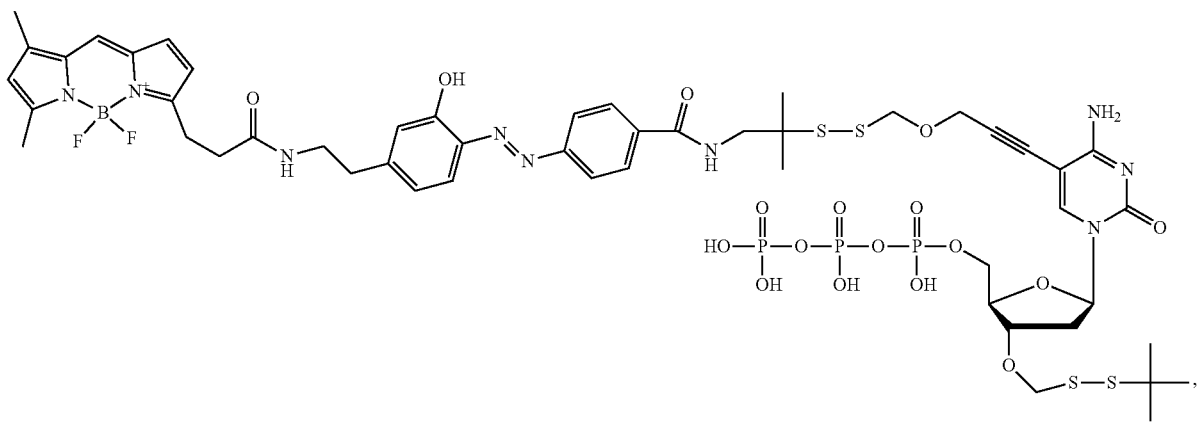

-continued
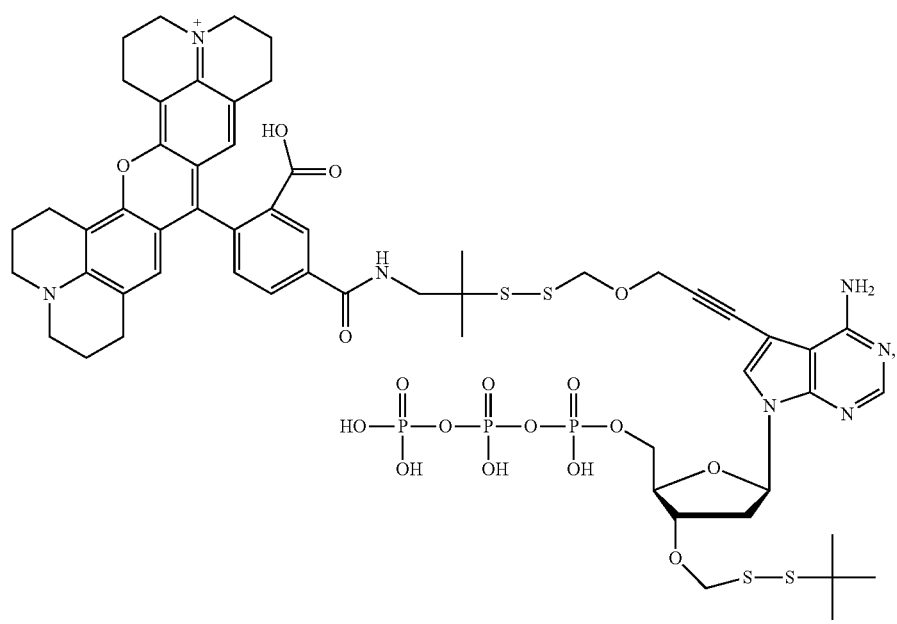
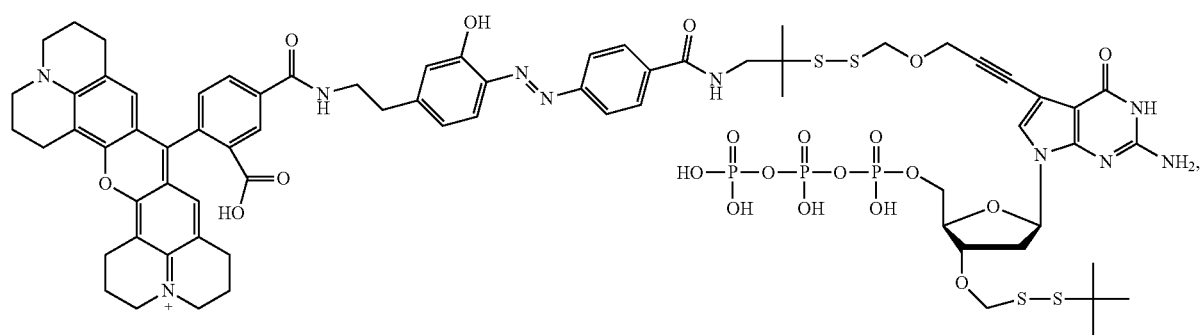
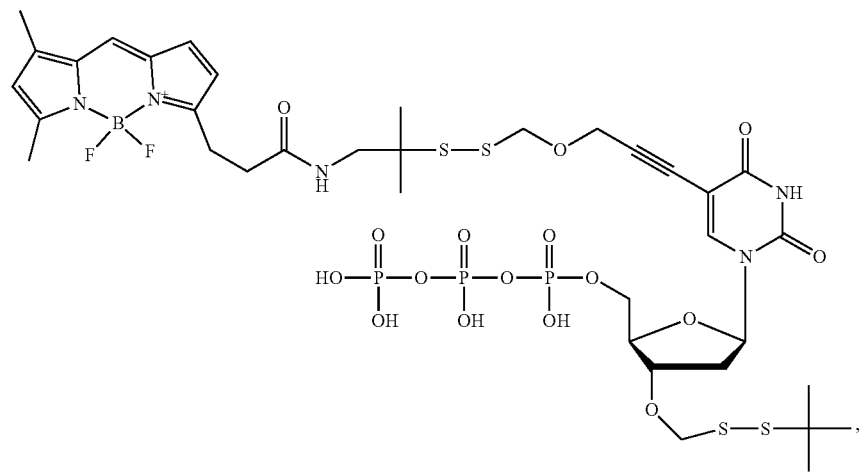

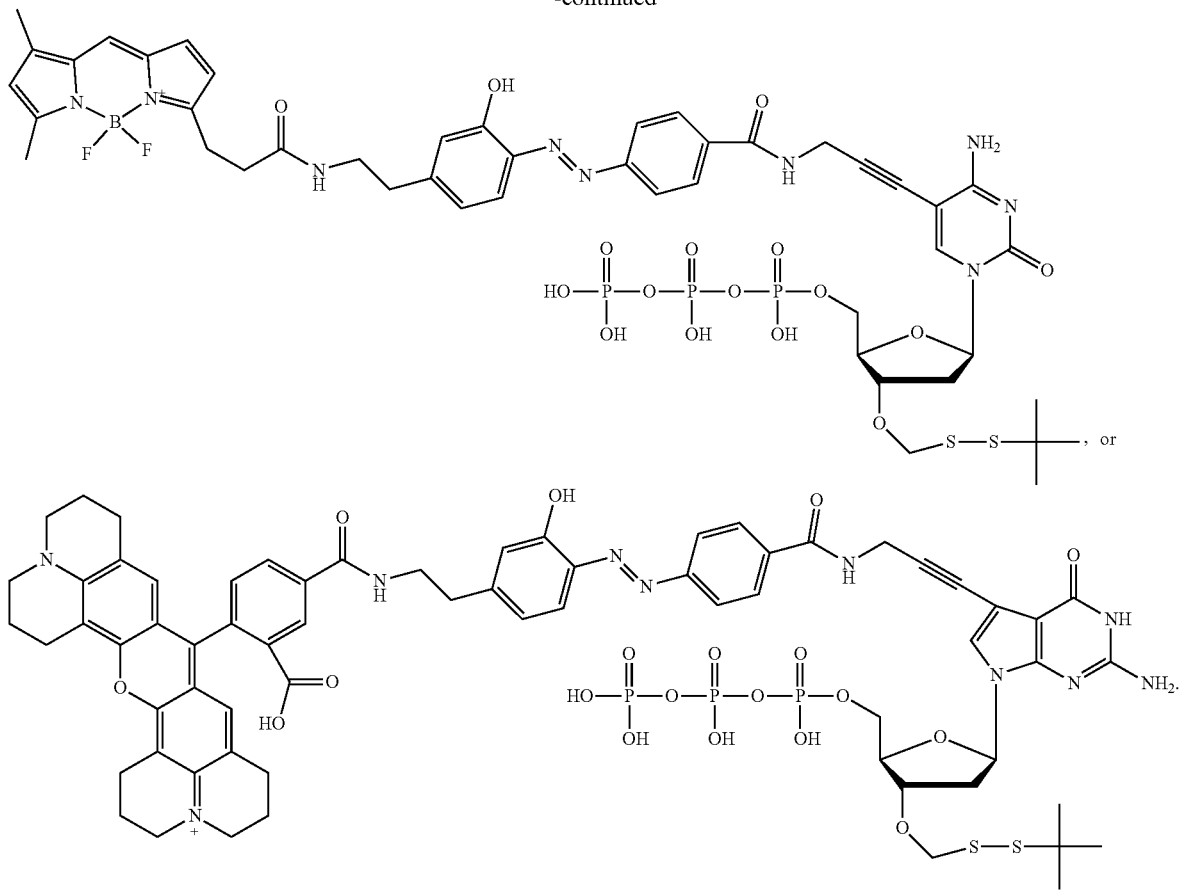

The subject invention provides a method for determining the nucleotide sequence of a single-stranded nucleic acid comprising:
a) contacting the single-stranded nucleic acid, with a nucleic acid polymerase and four types of tagged nucleotide analogues under conditions permitting the nucleic acid polymerase t-n catalyze incorporation of one of the tagged nucleotide analogues into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a nucleic acid extension product, wherein each type of the at least four types of tagged nucleotide analogues comprises: a base which is adenine, guanine, cytosine, thymine, or uracil, or a derivative of each thereof, a deoxyribose or ribose, and a cleavable blocking group bound to the 3'-oxygen of the deoxyribose or ribose that prevents the polymerase from catalyzing the incorporation of a subsequent nucleotide, and
(i) the first type of nucleotide analogue comprises a first type of base and a first type of detectable label bound to the base via a first type of linker;
(ii) the second type of nucleotide analogue comprises a second type of base and a second type of detectable label bound to the base via a second type of linker;
(iii) the third type of nucleotide analogue comprises a third type of base and the first type of detectable label bound to the base via the second type of linker; and
(iv) the fourth type of nucleotide analogue comprises a fourth type of base and the second type of detectable label bound to the base via the first type of linker;
wherein the first type and second type of linkers are different, and wherein the first type and second type of detectable label are different;
b) identifying whether a nucleotide analogue comprising the first type or second type of detectable label was incorporated in step (a);
c) contacting the incorporated tagged nucleotide analogue with a means of cleaving the first type of linker;
d) determining whether the label was removed by the means of cleaving in step (c) so as to thereby determine the identity of the incorporated nucleotide analogue;
e) contacting the incorporated tagged nucleotide analogue with a means of cleaving the second type of linker;
f) cleaving the 3'-oxygen blocking group so as to thereby form a 3'-OH;
g) iteratively performing steps (a)-(f) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product, so as to thereby determine the nucleotide sequence of the single-stranded nucleic acid.

The subject invention provides a method for determining the nucleotide sequence of a single-stranded nucleic acid comprising:
- a) contacting the single-stranded nucleic acid with a nucleic acid polymerase and a first type of tagged nucleotide analogue under conditions permitting the nucleic acid polymerase to catalyze incorporation of the tagged nucleotide analogue into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a DNA extension product, wherein the tagged nucleotide analogue comprises a first type of base which is adenine, guanine, cytosine, thymine, or uracil, or a derivative of each thereof, a deoxyribose or ribose, a cleavable blocking group bound to the 3'-oxygen of the deoxyribose or ribose that prevents the polymerase from catalyzing the incorporation of a subsequent nucleotide, and a first type of detectable label bound to the base via a first type of linker,
  and if a tagged nucleotide is not incorporated, iteratively repeating the contacting with a second, third, and fourth type of tagged nucleotide analogue until a tagged nucleotide analogue is incorporated, wherein
  (i) the second type of nucleotide analogue comprises a second type of base and a second type of detectable label bound to the base via a second type of linker;
  (ii) the third type of nucleotide analogue comprises a third type of base and the first type of detectable label bound to the base via the second type of linker; and
  (iii) the fourth type of nucleotide analogue comprises a fourth type of base and the second type of detectable label bound to the base via the first type of linker; wherein the first type and second type of linkers are different, and wherein the first type and second type of detectable label are different;
- b) identifying whether a nucleotide analogue comprising the first type or second type of detectable label was incorporated in step (a);
- c) contacting the incorporated nucleotide analogue with a means of cleaving the first type of linker;
- d) determining whether the detectable label was removed by the means of cleaving in step (c) so as to thereby determine the identity of the incorporated nucleotide analogue;
- e) contacting the incorporated tagged nucleotide analogue with a means of cleaving the second type of linker;
- f) cleaving the 3'-oxygen blocking group so as to thereby form a 3'-OH.
- g) iteratively performing steps (a)-(f) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product, so as to thereby determine the nucleotide sequence of the single-stranded nucleic acid.

The invention provides a method for determining the nucleotide sequence of a single-stranded nucleic acid comprising:
- a) contacting the single-stranded nucleic acid, with a nucleic acid polymerase and four types of tagged nucleotide analogues under conditions permitting the nucleic acid polymerase to catalyze incorporation of one of the tagged nucleotide analogues into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a nucleic acid extension product, wherein each type of the at least four types of tagged nucleotide analogues comprises: a base which is adenine, guanine, cytosine, thymine, or uracil, or a derivative of each thereof, a deoxyribose or ribose, and a blocking group bound to the 3'-oxygen of the deoxyribose or ribose that prevents the polymerase from catalyzing the incorporation of a subsequent nucleotide, and
  (i) the first type of nucleotide analogue comprises a first type of base and a first type of detectable label bound to the base via a first type of linker;
  (ii) the second type of nucleotide analogue comprises a second type of base and a second type of detectable label bound to the base via a second type of linker;
  (iii) the third type of nucleotide analogue comprises third type of base and the first type of detectable label bound to the base via the second type of linker; and
  (iv) the fourth type of nucleotide analogue comprises a fourth type of base and the second type of detectable label bound to the base via the first type of linker;
  and wherein the first type and second type of detectable label are different;
- b) contacting the single-stranded nucleic acid with four types of nucleotide reversible terminators, wherein each nucleotide reversible terminator comprises a blocking group to the 3'-oxygen of the deoxyribose or ribose that prevents the polymerase from catalyzing incorporation of a subsequent nucleotide, under conditions permitting the nucleic acid polymerase to catalyze incorporation of one of the nucleotide reversible terminators into the primer if:
  (i) the polymerase failed to incorporate a tagged nucleotide analogue in step a),
  (ii) the nucleotide reversible terminator is complementary to the nucleotide residue of the single-stranded nucleic acid which is immediately 5' to a nucleotide residue of the single-stranded nucleic acid hybridized to the 3' terminal nucleotide residue of the primer, and
- c) identifying whether a nucleotide analogue comprising the first type or second type of detectable label was incorporated in step (a);
- d) contacting the incorporated tagged nucleotide analogue with a means of cleaving the first type of linker;
- e) determining whether the label was removed by the means of cleaving in step (c) so as to thereby determine the identity of the incorporated nucleotide analogue;
- f) contacting the incorporated tagged nucleotide analogue with a means of cleaving the second type of linker;
- g) cleaving the 3'-oxygen blocking group so as to thereby form a 3'-OH;
- h) iteratively performing steps (a)-(g) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product, so as to thereby determine the nucleotide sequence of the single-stranded nucleic acid.

The invention provides a method for determining the nucleotide sequence of a single-stranded nucleic acid comprising:

a) contacting the single-stranded nucleic acid with a nucleic acid polymerase and a first type of tagged nucleotide analogue under conditions permitting the nucleic acid polymerase to catalyze incorporation of the tagged nucleotide analogue into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a DNA extension product, wherein the tagged nucleotide analogue comprises a first type of base which is adenine, guanine, cytosine, thymine, or uracil, or a derivative of each thereof, a deoxyribose or ribose, a blocking group bound to the 3'-oxygen of the deoxyribose or ribose that prevents the polymerase from catalyzing the incorporation of a subsequent nucleotide, and a first type of detectable label bound to the base via a first type of linker, and if a tagged nucleotide is not incorporated, iteratively repeating the contacting with a second, third, and fourth type of tagged nucleotide analogue until a tagged nucleotide analogue is incorporated, wherein (i) the second type of nucleotide analogue comprises a second type of base and a second type of detectable label bound to the base via a second type of linker;

(ii) the third type of nucleotide analogue comprises a third type of base and the first type of detectable label bound to the base via the second type of linker; and (iii) the fourth type of nucleotide analogue comprises a fourth type of base and the second type of detectable label bound to the base via the first type of linker;

wherein the first type and second type of linkers are different, and wherein the first type and second type of detectable label are different;

b) contacting the single-stranded nucleic acid with four types of nucleotide reversible terminators wherein each nucleotide reversible terminator comprises a blocking group to the 3'-oxygen of the deoxyribose or ribose that prevents the polymerase from catalyzing incorporation of a subsequent nucleotide, under conditions permitting the nucleic acid polymerase to catalyze incorporation of one of the nucleotide reversible terminators into the primer if:

(i) the polymerase failed to incorporate a tagged nucleotide analogue in step a), and (ii) the nucleotide reversible terminator is complementary to the nucleotide residue of the single-stranded nucleic acid which is immediately 5' to a nucleotide residue of the single-stranded nucleic acid hybridized to the 3' terminal nucleotide residue of the primer;

c) identifying whether a nucleotide analogue comprising the first type or second type of detectable label was incorporated in step (a);

d) contacting the incorporated nucleotide analogue with a means of cleaving the first type of linker;

e) determining whether the detectable label was removed by the means of cleaving in step (c) so as to thereby determine the identity of the incorporated nucleotide analogue;

f) contacting the incorporated tagged nucleotide analogue with a means of cleaving the second type of linker;

g) cleaving the 3'-oxygen blocking group so as to thereby form a 3'-OH.

h) iteratively performing steps (a)-(g) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product, so as to thereby determine the nucleotide sequence of the single-stranded nucleic acid.

In another embodiment, the 3'-oxygen blocking group of the nucleotide reversible terminators is bound to the 3'-oxygen by at least one orthogonal chemically cleavable linker. In another embodiment, the blocking group of the nucleotide reversible terminators comprises a dithiomethyl, azidomethyl, azo, allyl, and/or 2-nitrobenzl. In another embodiment, the blocking group of the nucleotide reversible terminators comprises an alkyldithiomethyl. In another embodiment, the blocking group of the nucleotide reversible terminators is chemically cleaved or photocleaved. In another embodiment, the blocking group of the nucleotide reversible terminators is cleaved by a water soluble phosphine, thereby resulting in a 3'-OH. In another embodiment, the water soluble phosphine is tris-(2-carboxyethyl)phosphine (TCEP) or tris (hydroxypropyl) phosphine (THP).

In another embodiment, the nucleotide reversible terminators are 3'-O-SS(DTM)-dNTPs (3'-O-t-Butyldithiomethyl (SS)-dATP, 3'-O-t-Butyldithiomethyl(SS)-dCTP, 3'-O-t-Butyldithiomethyl(SS)-dTTP and 3'-O-t-Butyldithiomethyl (SS)-dGTP).

In another embodiment, the blocking group of the nucleotide reversible terminators is cleaved by sodium dithionite.

In another embodiment, the 3'-oxygen blocking group of the tagged nucleotide analogues is bound to the 3'-oxygen by at least one orthogonal chemically cleavable linker. In another embodiment, the blocking group of the tagged nucleotide analogues comprises a dithiomethyl, azidomethyl, azo, allyl, and/or 2-nitrobenzl. In another embodiment, the blocking group of the tagged nucleotide analogues comprises an alkyldithiomethyl.

In another embodiment, the base of one or more of the first, second, third, and/or fourth type of nucleotide analogue comprise a deazapurine base.

In another embodiment the first base is A, or derivative thereof and:

(i) the second base is T/U or a derivative thereof, the third base is C or a derivative thereof, and the fourth base is G or a derivative thereof, (ii) the second base is T/U or a derivative thereof, the third base is G or a derivative thereof, and the fourth base is C or a derivative thereof, (iii) the second base is C or a derivative thereof, the third base is T/U or a derivative thereof, and the fourth base is G or a derivative thereof,
(iv) the second base is C or a derivative thereof, the third base is G or a derivative thereof, and the fourth base is T/U or a derivative thereof,
(v) the second base is G or a derivative thereof, the third base is T/U or a derivative thereof, and the fourth base is C or a derivative thereof, or
(vi) the second base is G or a derivative thereof, the third base is C or a derivative thereof, and the fourth base is T/U or a derivative thereof.

In another embodiment the first base is T/U, or derivative thereof and:
(i) the second base is C or a derivative thereof, the third base is A or a derivative thereof, and the fourth base is G or a derivative thereof,
(ii) the second base is C or a derivative thereof, the third base is G or a derivative thereof, and the fourth base is A or a derivative thereof,
(iii) the second base is A or a derivative thereof, the third base is C or a derivative thereof, and the fourth base is G or a derivative thereof,
(iv) the second base is A or a derivative thereof, the third base is G or a derivative thereof, and the fourth base is C or a derivative thereof,
(v) the second base is G or a derivative thereof, the third base is C or a derivative thereof, and the fourth base is A or a derivative thereof, or
(vi) the second base is G or a derivative thereof, the third base is A or a derivative thereof, and the fourth base is C or a derivative thereof.

In another embodiment, the first base is C, or derivative thereof and:
(i) the second base is A or a derivative thereof, the third base is T/U or a derivative thereof, and the fourth base is G or a derivative thereof,
(ii) the second base is A or a derivative thereof, the third base is G or a derivative thereof, and the fourth base is T/U or a derivative thereof,
(iii) the second base is T/U or a derivative thereof, the third base is A or a derivative thereof, and the fourth base is G or a derivative thereof,
(iv) the second base is T/U or a derivative thereof, the third base is G or a derivative thereof, and the fourth base is A or a derivative thereof,
(v) the second base is G or a derivative thereof, the third base is T/U or a derivative thereof, and the fourth base is A or a derivative thereof, or
(vi) the second base is G or a derivative thereof, the third base is A or a derivative thereof, and the fourth base is T/U or a derivative thereof.

In another embodiment first base is G, or derivative thereof and:
(i) the second base is C or a derivative thereof, the third base is T/U or a derivative thereof, and the fourth base is A or a derivative thereof,
(ii) the second base is C or a derivative thereof, the third base is A or a derivative thereof, and the fourth base is T/U or a derivative thereof,
(iii) the second base is T/U or a derivative thereof, the third base is A or a derivative thereof, and the fourth base is C or a derivative thereof,
(iv) the second base is T/U or a derivative thereof, the third base is C or a derivative thereof, and the fourth base is A or a derivative thereof,
(v) the second base is A or a derivative thereof, the third base is T/U or a derivative thereof, and the fourth base is C or a derivative thereof, or
(vi) the second base is A or a derivative thereof, the third base is C or a derivative thereof, and the fourth base is T/U or a derivative thereof.

In another embodiment, the first type of linker and/or second type of linker comprises orthogonal chemically cleavable linkers.

In another embodiment, first and/or second type of linkers comprise one or more of an alkyldithiomethyl linker, an azo linker, an allyl linker, a nitrobenzyl linker, an azidomethyl linker, and/or a dimethyl ketal linker.

In another embodiment, the first and/or second type of linkers are chemically cleavable or photocleavable. In another embodiment, the first and/or second type of linker are cleavable by a water soluble phosphine, thereby resulting in a 3'-OH. In another embodiment, the water soluble phosphine is tris-(2-carboxyethyl)phosphine (TCEP) or tris (hydroxypropyl)phosphine (THP). In another embodiment, the first and/or second type of linkers can be cleaved by sodium dithionite.

In another embodiment, the first and/or second type of detectable label is one or more of a dye, a fluorophore, a fluorescence energy transfer tag, a chemiluminescent compound, a chromophore, a mass tag, an electrophore, a mononucleotide, an oligonucleotide, or a combination thereof. In another embodiment, the first and/or second type of detectable label is a fluorophore. In another embodiment, the first and/or second type of detectable label is BodipyFL, R6G, ROX, Cy5, or Alexa488. In another embodiment, the tagged nucleotides are selected from the group comprising one or more of 3'-O-SS-dATP-7-SS-Rox, 3'-O-SS-dTTP-5-SS-BodipyFL, 3'-O-SS-dGTP-7-Azo-Rox or 3'-O-SS-dCTP-5-Azo-BodipyFL.

In another embodiment, the first type of linker is an alkyldithiomethyl linker and the second type of linker is an azo linker.

In another embodiment, the tagged nucleotide analogues are selected from the group comprising:

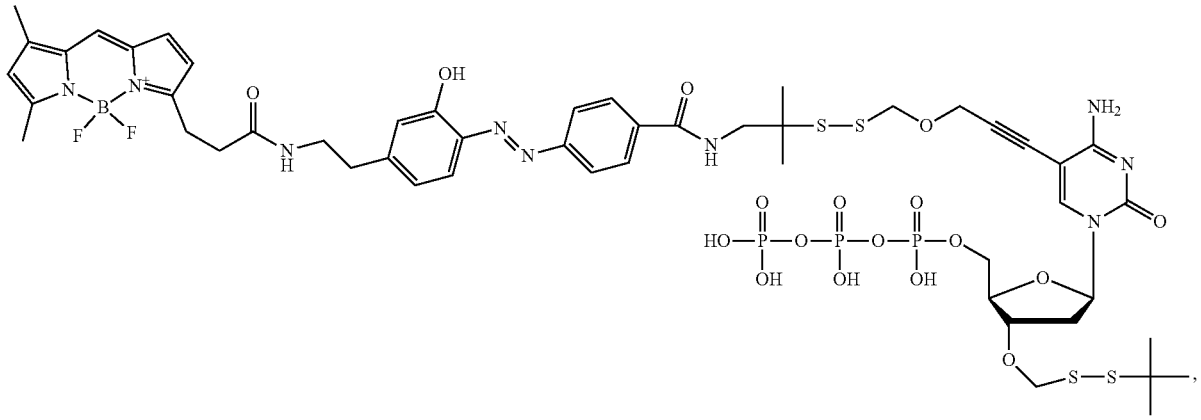

-continued
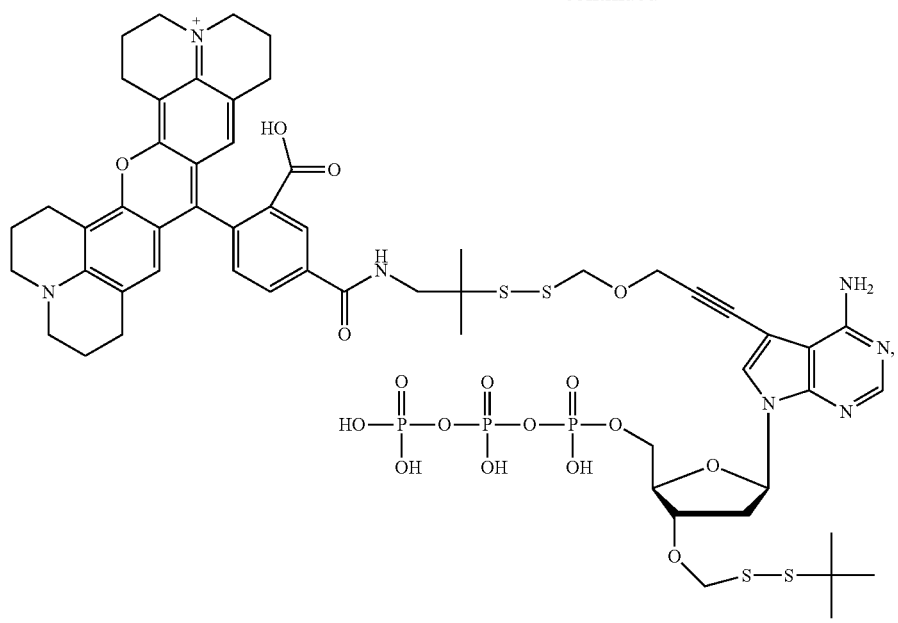
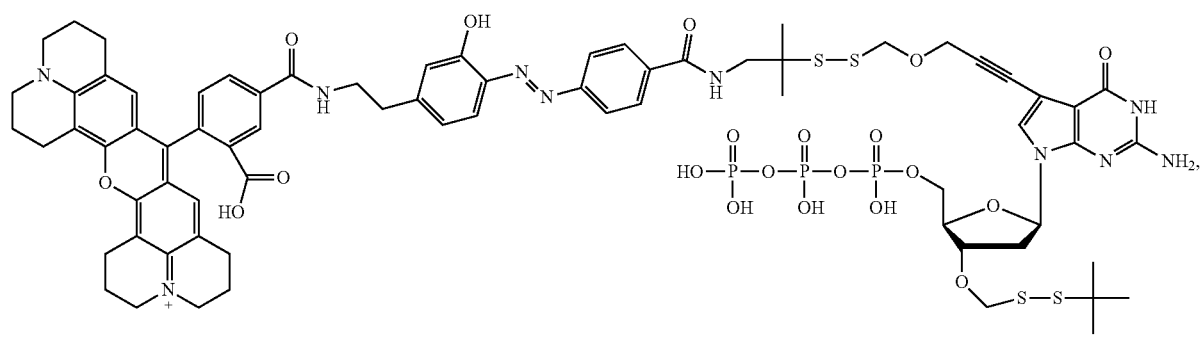
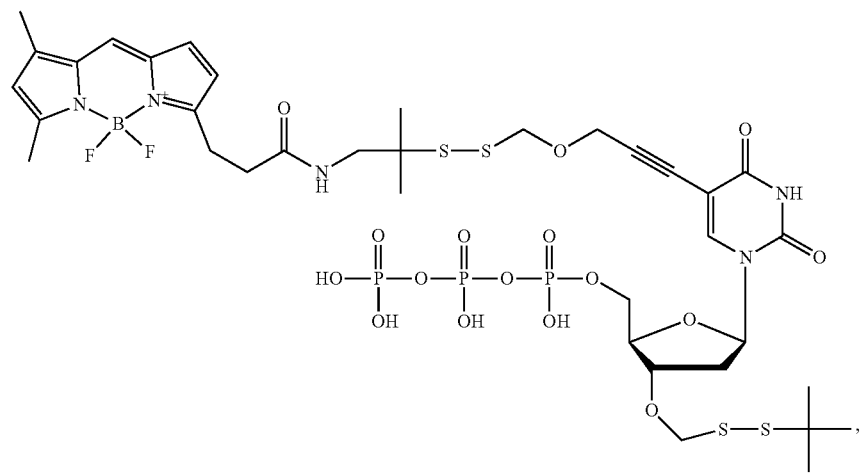

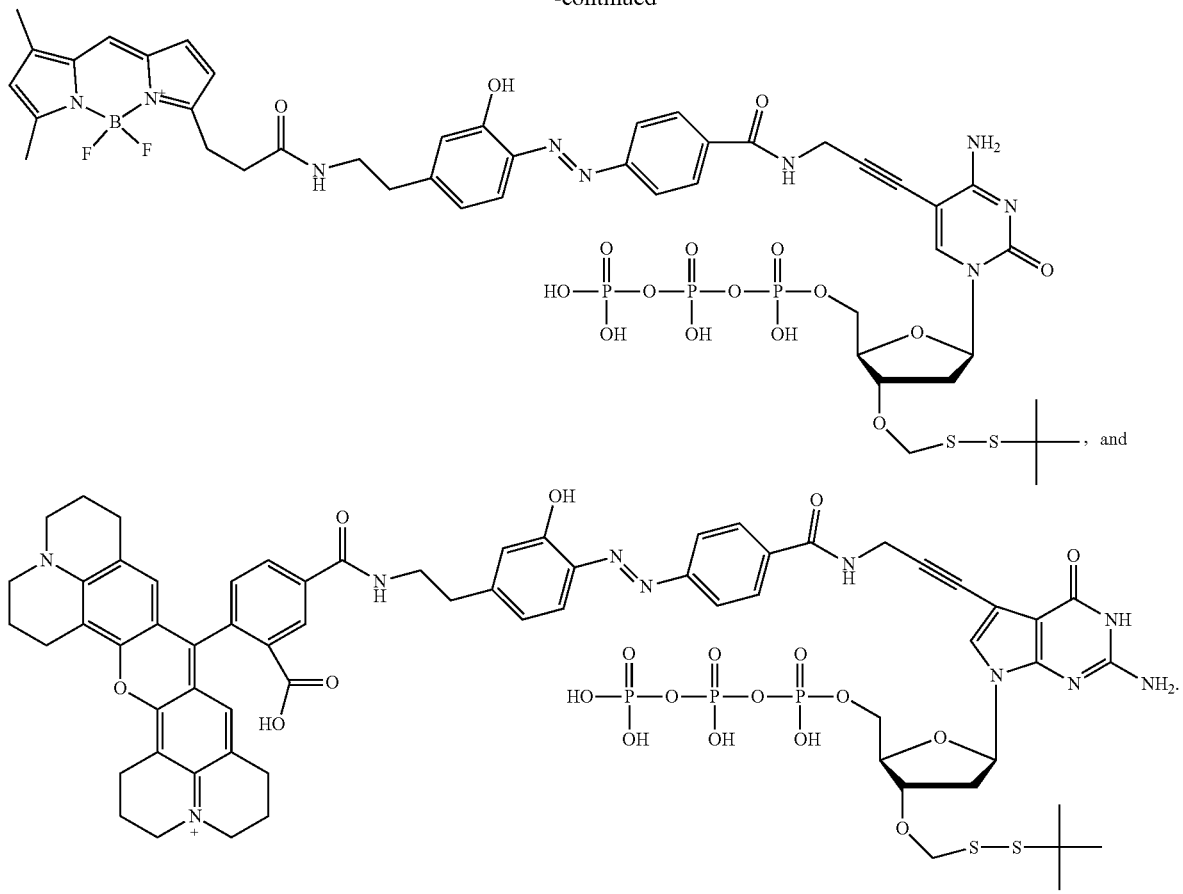

The invention also provides a kit for nucleic acid sequencing, comprising, in separate compartments:
a) Four types of tagged nucleotide analogue, wherein each type of tagged nucleotide analogue comprises a base selected from the group consisting of A, T, C, G, or U or derivatives thereof, a deoxyribose or ribose, and a blocking group bound to the 3'-oxygen of the deoxyribose or ribose, and
  (i) the first type of nucleotide analogue comprises a first type of detectable label bound to the base via a first type of linker;
  (ii) the second type of nucleotide analogue comprises a second type of detectable label bound to the base via a second type of linker;
  (iii) the third type of nucleotide analogue comprises the first type of detectable label bound to the base via the second type of linker; and
  (iv) the fourth type of nucleotide analogue comprises the second type of detectable label bound to the base via the first type of linker;
  wherein each type of nucleotide has a different base, the first type and second type of linker are different, and the first type and second type of detectable label are different
b) reagents suitable for use in nucleic acid polymerization; and
c) instructions for use.

In another embodiment, the first type of linker is a cleavable allyl linker and the second type of linker is a cleavable azo linker or a dithiomethyl linker.

In another embodiment the kit further comprises four types of nucleotide reversible terminator, wherein each nucleotide reversible terminator comprises a blocking group to the 3'-oxygen of the deoxyribose or ribose that prevents the polymerase from catalyzing incorporation of a subsequent nucleotide.

In another embodiment the first base is A, or derivative thereof and:
  (i) the second base is T/U or a derivative thereof, the third base is C or a derivative thereof, and the fourth base is G or a derivative thereof,
  (ii) the second base is T/U or a derivative thereof, the third base is G or a derivative thereof, and the fourth base is C or a derivative thereof,
  (iii) the second base is C or a derivative thereof, the third base is T/U or a derivative thereof, and the fourth base is G or a derivative thereof,
  (iv) the second base is C or a derivative thereof, the third base is G or a derivative thereof, and the fourth base is T/U or a derivative thereof,
  (v) the second base is G or a derivative thereof, the third base is T/U or a derivative thereof, and the fourth base is C or a derivative thereof, or
  (vi) the second base is G or a derivative thereof, the third base is C or a derivative thereof, and the fourth base is T/U or a derivative thereof.

In another embodiment the first base is T/U, or derivative thereof and:
  (i) the second base is C or a derivative thereof, the third base is A or a derivative thereof, and the fourth base is G or a derivative thereof, (ii) the second base is C or a derivative thereof, the third base is G or a derivative thereof, and the fourth base is A or a derivative thereof,
(iii) the second base is A or a derivative thereof, the third base is C or a derivative thereof, and the fourth base is G or a derivative thereof,
(iv) the second base is A or a derivative thereof, the third base is G or a derivative thereof, and the fourth base is C or a derivative thereof,
(v) the second base is G or a derivative thereof, the third base is C or a derivative thereof, and the fourth base is A or a derivative thereof, or
(vi) the second base is G or a derivative thereof, the third base is A or a derivative thereof, and the fourth base is C or a derivative thereof.

In another embodiment, the first base is C, or derivative thereof and:
(i) the second base is A or a derivative thereof, the third base is T/U or a derivative thereof, and the fourth base is G or a derivative thereof,
(ii) the second base is A or a derivative thereof, the third base is G or a derivative thereof, and the fourth base is T/U or a derivative thereof,
(iii) the second base is T/U or a derivative thereof, the third base is A or a derivative thereof, and the fourth base is G or a derivative thereof,
(iv) the second base is T/U or a derivative thereof, the third base is G or a derivative thereof, and the fourth base is A or a derivative thereof,
(v) the second base is G or a derivative thereof, the third base is T/U or a derivative thereof, and the fourth base is A or a derivative thereof, or
(vi) the second base is G or a derivative thereof, the third base is A or a derivative thereof, and the fourth base is T/U or a derivative thereof.

In another embodiment first base is G, or derivative thereof and:
(i) the second base is C or a derivative thereof, the third base is T/U or a derivative thereof, and the fourth base is A or a derivative thereof,
(ii) the second base is C or a derivative thereof, the third base is A or a derivative thereof, and the fourth base is T/U or a derivative thereof,
(iii) the second base is T/U or a derivative thereof, the third base is A or a derivative thereof, and the fourth base is C or a derivative thereof,
(iv) the second base is T/U or a derivative thereof, the third base is C or a derivative thereof, and the fourth base is A or a derivative thereof,
(v) the second base is A or a derivative thereof, the third base is T/U or a derivative thereof, and the fourth base is C or a derivative thereof, or
(vi) the second base is A or a derivative thereof, the third base is C or a derivative thereof, and the fourth base is T/U or a derivative thereof.

The invention provides a nucleotide analogue comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker or alternative cleavable linker such as Azo.

The invention also provides a composition comprising four different types of the above nucleotide analogues with an alkyldithiomethyl bound to the 3'-oxygen of the deoxyribose or ribose: (1) a nucleotide comprising a cleavable Azo linker between the base and Dye1; (2) a nucleotide comprising a cleavable Azo linker between the base and Dye2; (3) a nucleotide comprising a cleavable DTM linker between the base and Dye1; and (4) a nucleotide comprising a cleavable DTM linker between the base and Dye2.

The invention also provides a method for sequencing a nucleic acid, comprising:
a) providing
1) a nucleic acid,
2) a nucleic acid polymerase,
3) a primer capable of hybridizing to said nucleic acid, and
4) four different labeled nucleotide analogues, each comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker or an Azo linker, and four orthologous combinations of dye and cleavable linker: (1) cleavable Azo linker and Dye1; (2) cleavable Azo linker and Dye2; (3) cleavable DTM linker and Dye1; and (4) cleavable DTM linker and Dye2;
b) incorporating with said nucleic acid polymerase one or more of said nucleotide analogues into said primer to create an extension strand;
c) detecting said unique detectable label of each incorporated nucleotide analogue, so as to thereby identify each incorporated nucleotide analogue in said extension strand in two steps,
1) imaging after incorporation to provide two possible nucleotides,
2) imaging after cleavage of the Azo linker with sodium dithionite to determine the precise nucleotide incorporated;
d) cleaving the DTM cleavable linker to any remaining Dye and DTM blocking group on the 3'-OH in preparation for the next cycle; and
e) repeating steps a) to d);
thereby sequencing the nucleic acid.

The invention also provides a kit for nucleic acid sequencing, comprising, in separate compartments:
a) a plurality of nucleotide analogues, each comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker or an Azo linker, and four orthologous combinations of dye and cleavable linker: (1) cleavable Azo linker and Dye1; (2) cleavable Azo linker and Dye2; (3) cleavable DTM linker and Dye1; and (4) cleavable DTM linker and Dye2;
b) reagents suitable for use in nucleic acid polymerization; and
c) instructions for use.

The invention provides a nucleotide analogue comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker or alternative cleavable linker such as Azo.

The invention also provides a composition comprising four different types of the above nucleotide analogues with an alkyldithiomethyl bound to the 3'-oxygen of the deoxyribose or ribose: (1) a nucleotide comprising a cleavable Azo linker between the base and Dye1; (2) a nucleotide comprising a cleavable Azo linker between the base and Dye2; (3) a nucleotide comprising a cleavable DTM linker between the base and Dye1; and (4) a nucleotide comprising a cleavable DTM linker between the base and Dye2.

The invention also provides a method for sequencing a nucleic acid, comprising:
a) providing
1) a nucleic acid,
2) a nucleic acid polymerase,
3) a primer capable of hybridizing to said nucleic acid, and
4) four different labeled nucleotide analogues, each comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker or an Azo linker, and four orthologous combinations of dye and cleavable linker: (1) cleavable 2-nitrobenzyl (2NB) linker and Dye1; (2) cleavable 2NB linker and Dye2; (3) cleavable DTM linker and Dye1; and (4) cleavable DTM linker and Dye2;
b) incorporating with said nucleic acid polymerase one or more of said nucleotide analogues into said primer to create an extension strand;
c) detecting said unique detectable label of each incorporated nucleotide analogue, so as to thereby identify each incorporated nucleotide analogue in said extension strand in two steps,
1) imaging after incorporation to provide two possible nucleotides,
2) imaging after photocleavage of the 2-nitrophenyl linker with 340 nm light to determine the precise nucleotide incorporated;
d) cleaving the DTM cleavable linker to any remaining Dye and DTM blocking group on the 3'-OH in preparation for the next cycle; and
e) repeating steps a) to d);
thereby sequencing the nucleic acid.

The invention also provides a kit for nucleic acid sequencing, comprising, in separate compartments:
a) a plurality of nucleotide analogues, each comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker or a 2-nitrobenzyl (2NB) linker, and four orthologous combinations of dye and cleavable linker: (1) cleavable 2NB linker and Dye1; (2) cleavable 2NB linker and Dye2; (3) cleavable DTM linker and Dye1; and (4) cleavable DTM linker and Dye2;
b) reagents suitable for use in nucleic acid polymerization; and
c) instructions for use.

The invention provides a nucleotide analogue comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker or alternative cleavable linker such as Azo.

The invention also provides a composition comprising four different types of the above nucleotide analogues with an alkyldithiomethyl bound to the 3'-oxygen of the deoxyribose or ribose: (1) a nucleotide comprising a cleavable 2-nitrobenzyl (2NB) linker between the base and Dye1; (2) a nucleotide comprising a cleavable 2NB linker between the base and Dye2; (3) a nucleotide comprising a cleavable DTM linker between the base and Dye1; and (4) a nucleotide comprising a cleavable DTM linker between the base and Dye2.

The invention also provides a method for sequencing a nucleic acid, comprising:
a) providing
1) a nucleic acid,
2) a nucleic acid polymerase,
3) a primer capable of hybridizing to said nucleic acid, and
4) four different labeled nucleotide analogues, each comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker or an Azo linker, and four orthologous combinations of dye and cleavable linker: (1) cleavable allyl linker and Dye1; (2) cleavable allyl linker and Dye2; (3) cleavable DTM linker and Dye1; and (4) cleavable DTM linker and Dye2;
b) incorporating with said nucleic acid polymerase one or more of said nucleotide analogues into said primer to create an extension strand;
c) detecting said unique detectable label of each incorporated nucleotide analogue, so as to thereby identify each incorporated nucleotide analogue in said extension strand in two steps,
(i) imaging after incorporation to provide two possible nucleotides
(ii) imaging after cleavage of the allyl linker with Pd(0) to determine the precise nucleotide incorporated;
d) cleaving the DTM cleavable linker to any remaining Dye and DTM blocking group on the 3'-OH in preparation for the next cycle; and
e) repeating steps a) to d);
thereby sequencing the nucleic acid.

The invention also provides a kit for nucleic acid sequencing, comprising, in separate compartments:
a) a plurality of nucleotide analogues, each comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker or an Azo linker, and four orthologous combinations of dye and cleavable linker: (1) cleavable allyl linker and Dye1; (2) cleavable allyl linker and Dye2; (3) cleavable DTM linker and Dye1; and (4) cleavable DTM linker and Dye2;
b) reagents suitable for use in nucleic acid polymerization; and
c) instructions for use.

Experimental Discussion

Scheme 1:
Use of 3'-O-SS(DTM)-dNTP-SS-Dyes (3'-O-SS-dATP-7-SS-Rox, 3'-O-SS-dTTP-5-SS-BodipyFL, 3'-O-SS-dGTP-7-Azo-Rox and 3'-O-SS-dCTP-5-Azo-BodipyFL) to perform 2-color DNA SBS.

Step 1, Addition of DNA polymerase and the four nucleotide analogues (3'-O-SS-dATP-7-SS-Rox, 3'-O-SS-dTTP-5-SS-BodipyFL, 3'-O-SS-dGTP-7-Azo-Rox and 3'-O-SS-dCTP-5-Azo-BodipyFL) to the immobilized primed DNA template enables the incorporation of the complementary nucleotide analogue to the growing DNA strand to terminate DNA synthesis.

Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye.

Step 3, after washing away the unincorporated dye labeled nucleotides, detection of the unique fluorescence signal from each of the fluorescent dyes on the DNA products allows the identification of the incorporated nucleotide for sequence determination, Rox signal indicates incorporation of both A and G, BodipyFL signal indicates incorporation of T and C.

Step 4, cleavage of Azo linker by adding sodium dithionite (Na2S2O4) to the elongated DNA strands results in removal of Rox from incorporated G and BodipyFL from incorporated C.

Figure 1B:
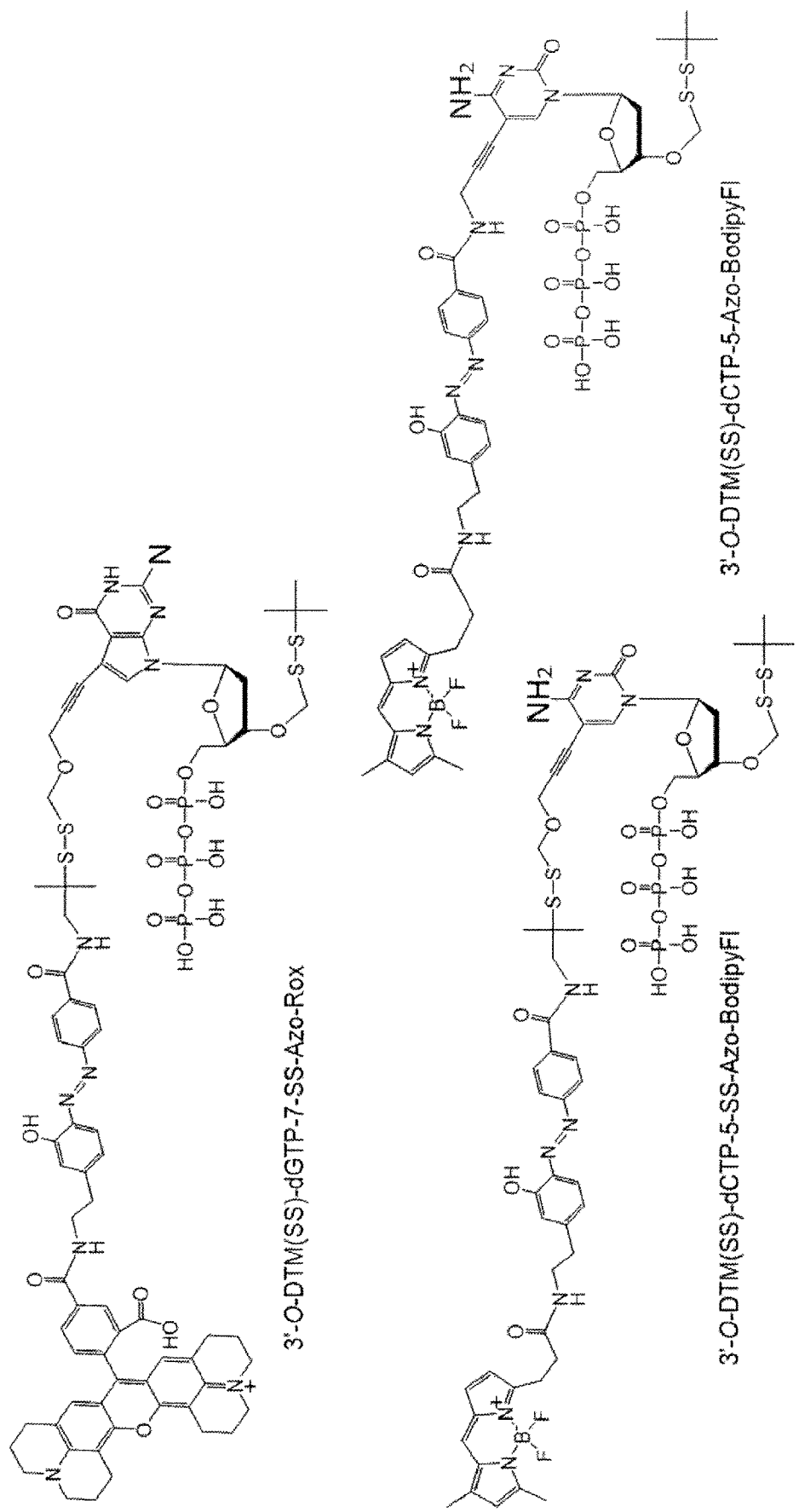
Figure 2A:
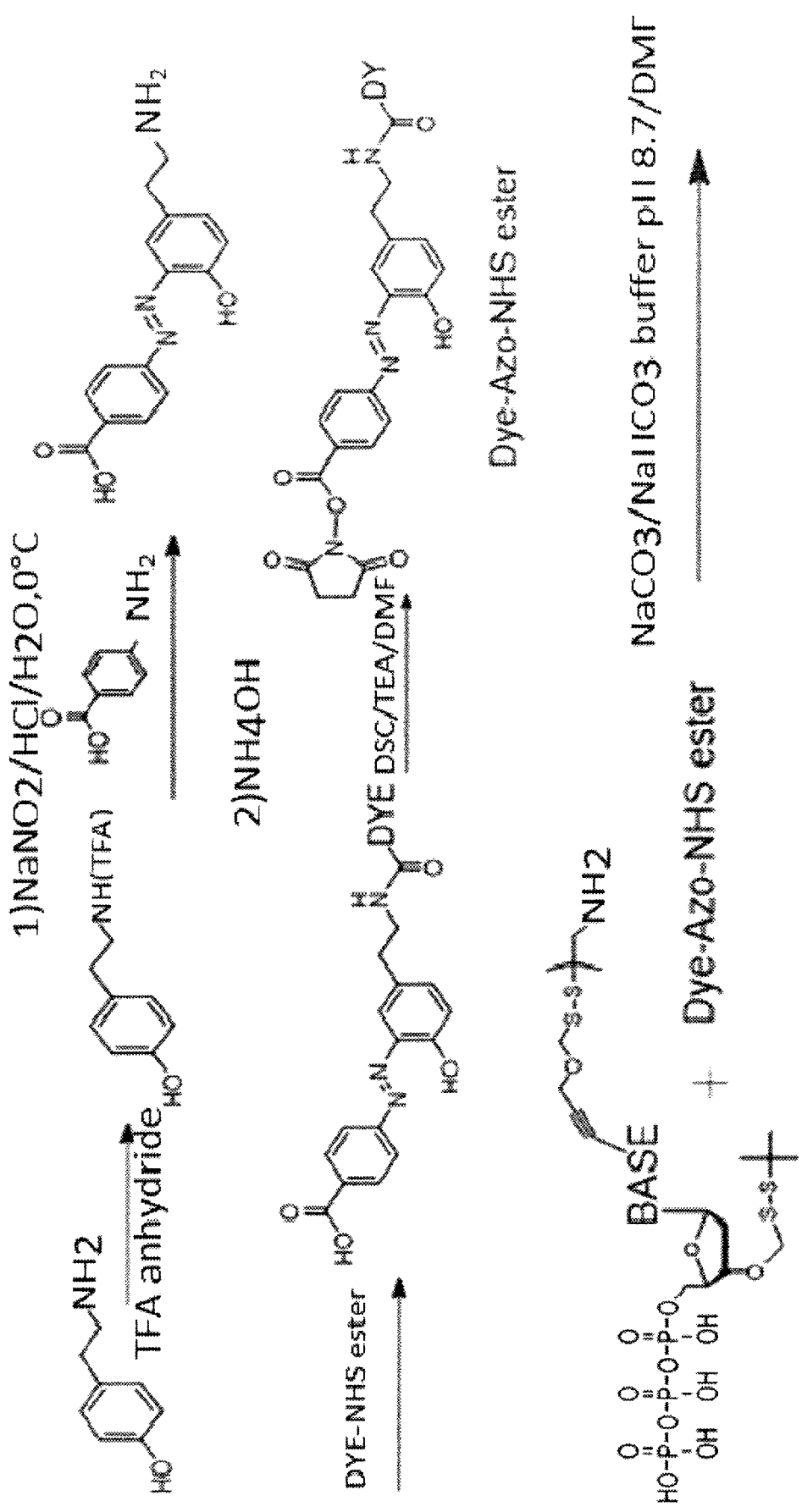
FIG. 2: Synthesis of Azo Linker and general method to synthesize 3'-O-SS(DTM)-dNTP-SS-Azo-Dye. The amino acid derivative of the Azo linker molecule is synthesized using the well-established diazonium coupling reaction. The resulting compound is coupled with Dye NHS ester giving the dye labeled acid derivative of the Azo linker, which can be further converted to the NHS ester by treatment with DSC and TEA. The product is then coupled to the amino group of 3'-O-SS(DTM)-dNTP-SS-NH$_2$ yielding 3'-O-SS(DTM)-dNTP-SS-Azo-Dye.
Figure 2B:
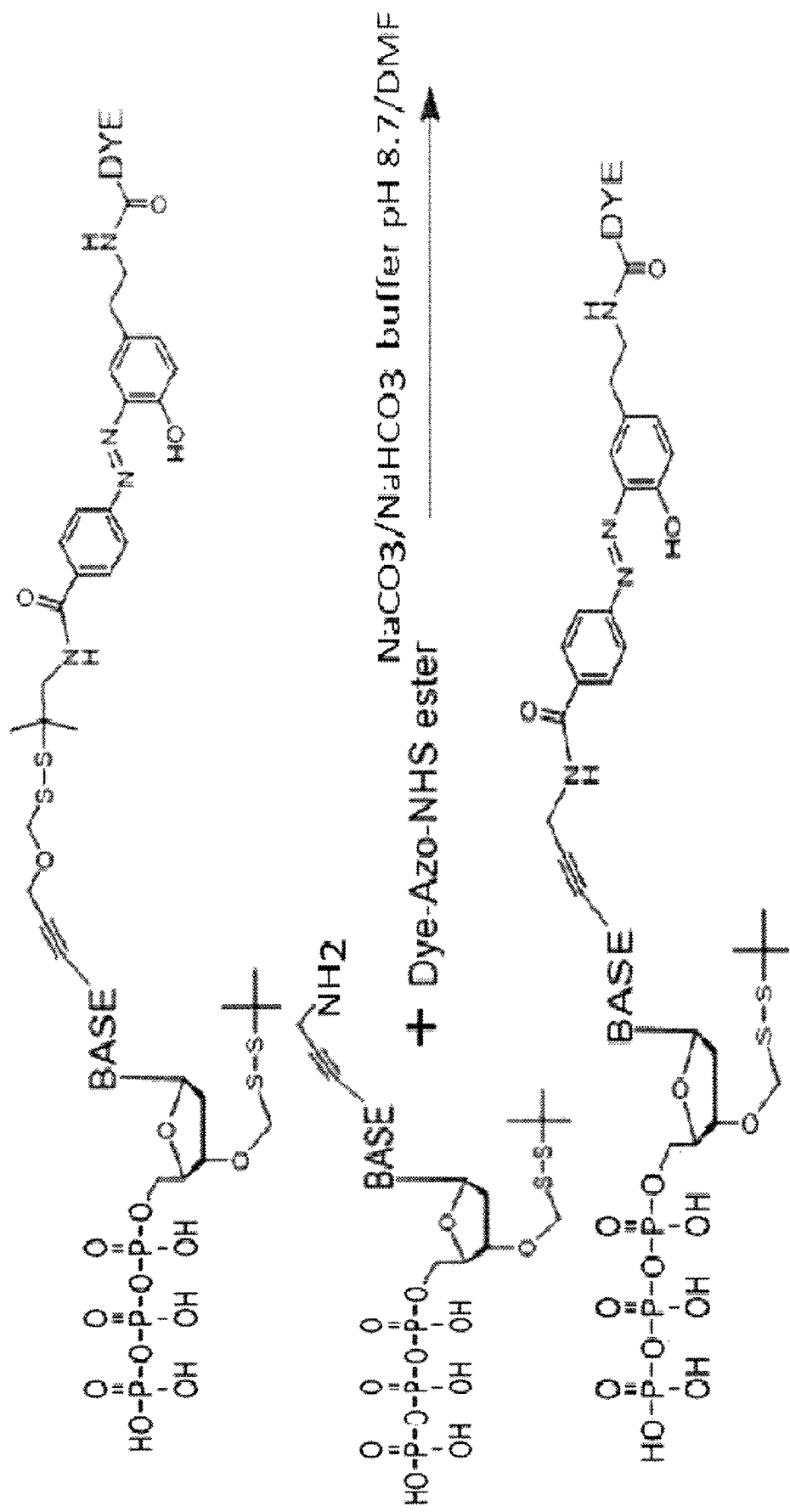
Figure 3A:
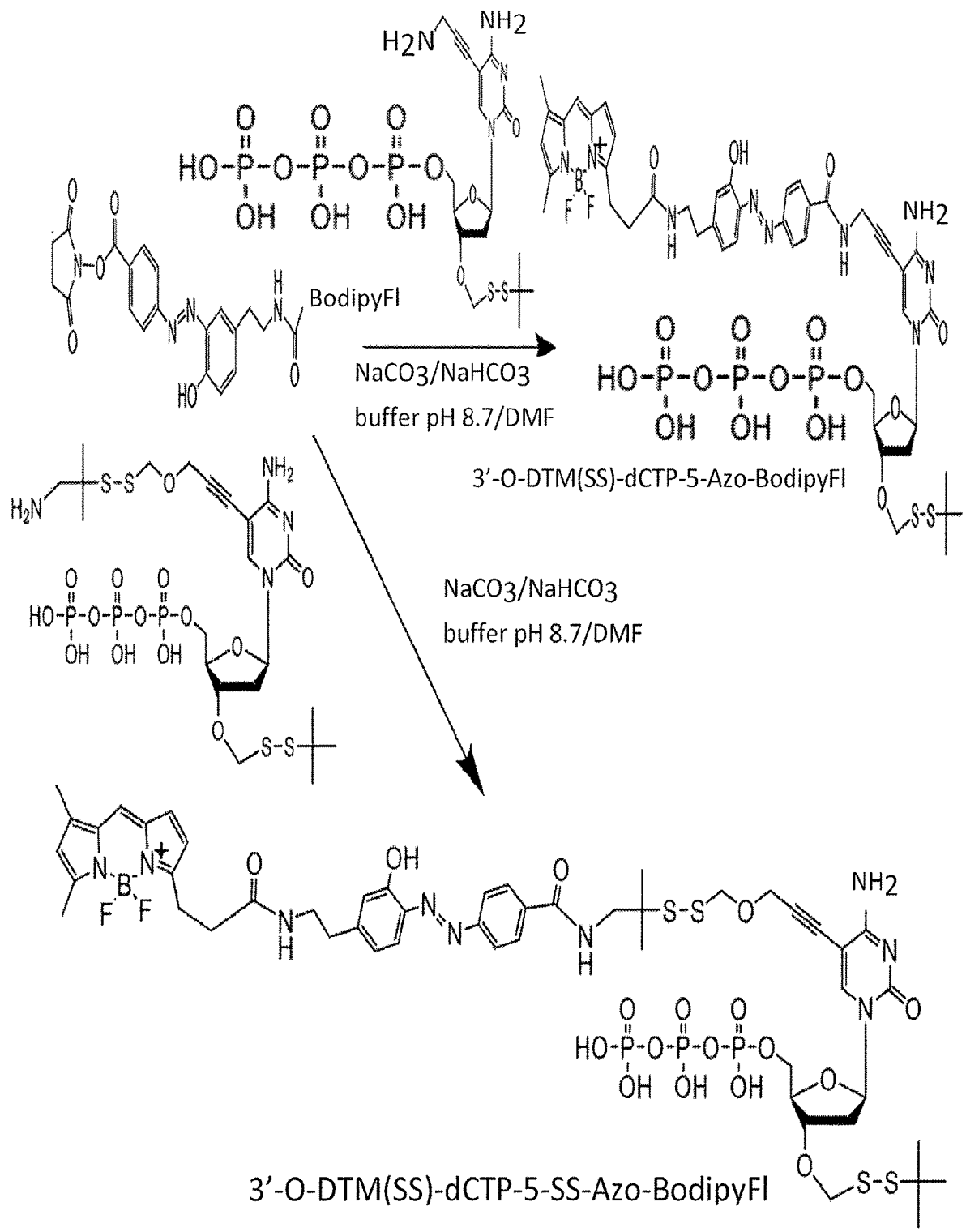
FIG. 3: Example synthesis of 3'-O-SS(DTM)-dGTP-SS-Azo-Rox and 3'-O-SS(DTM)-dTTP-SS-Azo-BodipyFL. Rox and BodipyFL labeled Azo Linker NHS esters are coupled with 3'-O-SS(DTM)-dGTP-SS-NH$_2$ and 3'-O-SS(DTM)-dTTP-SS-NH$_2$ giving 3'-O-SS(DTM)-dGTP-SS-Azo-Rox and 3'-O-SS(DTM)-dTTP-SS-Azo-BodipyFL.
Figure 3B:
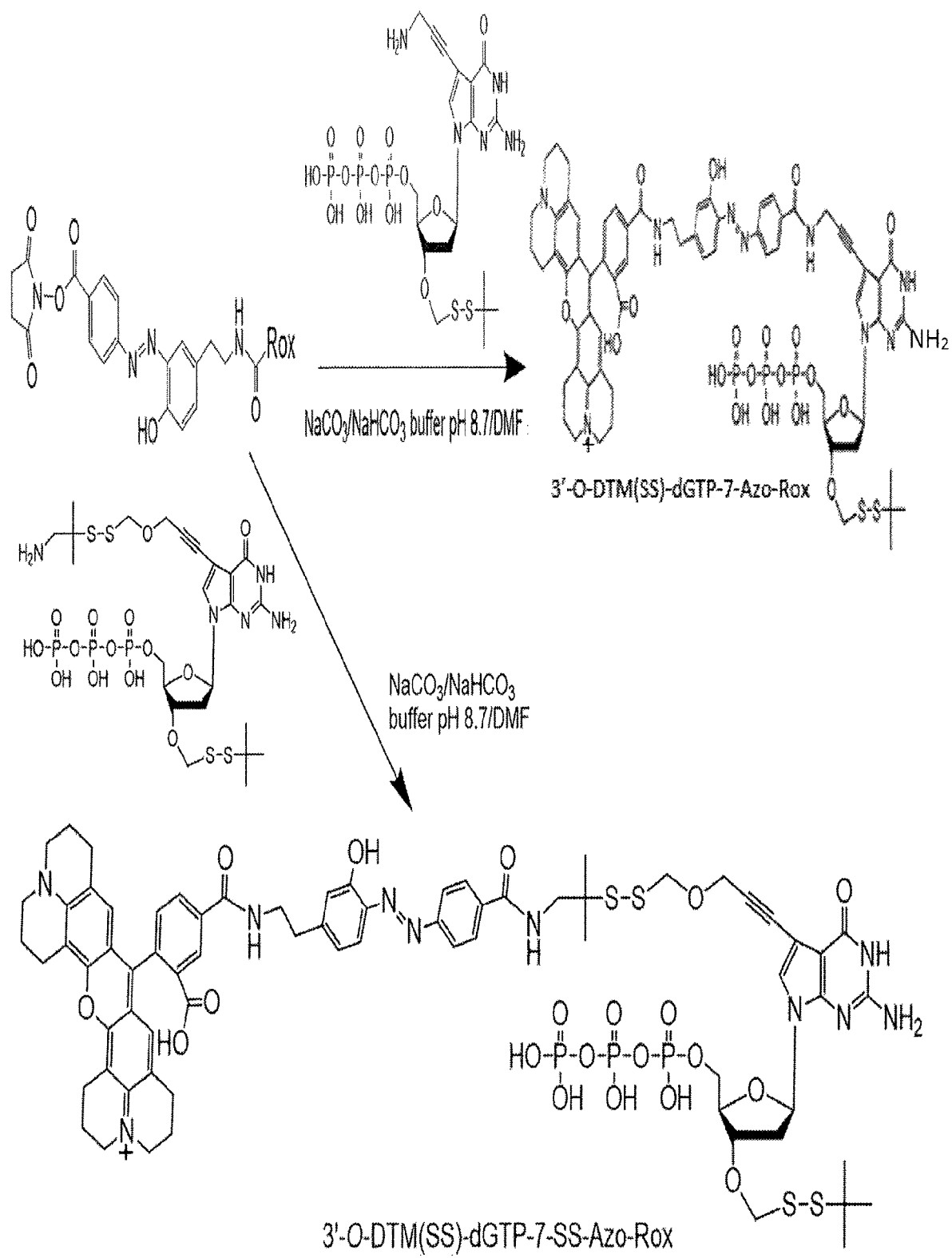
Figure 4:
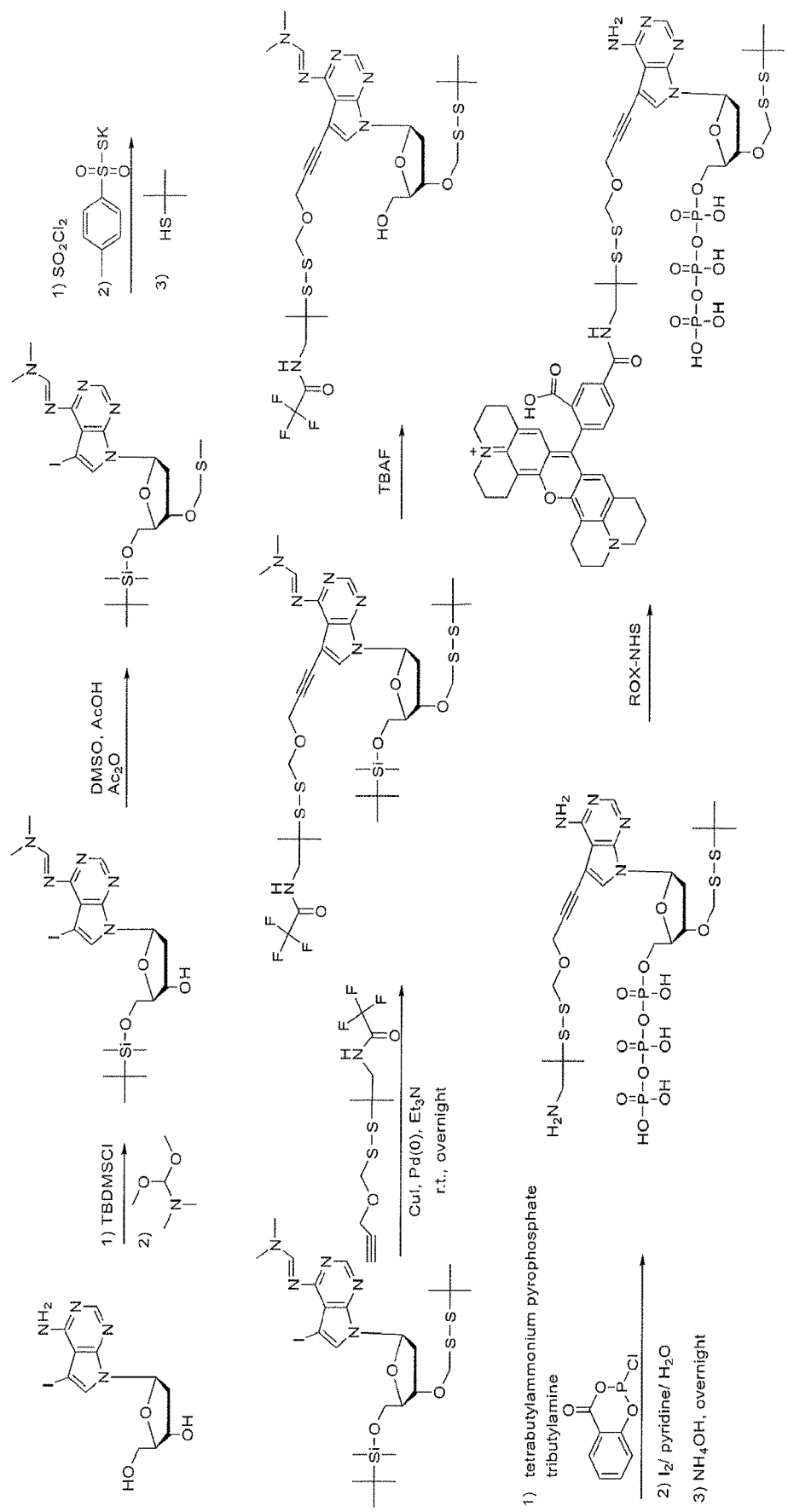
FIG. 4: Synthesis of 3'-O-SS(DTM)-dATP-SS-Rox.
Figure 5:
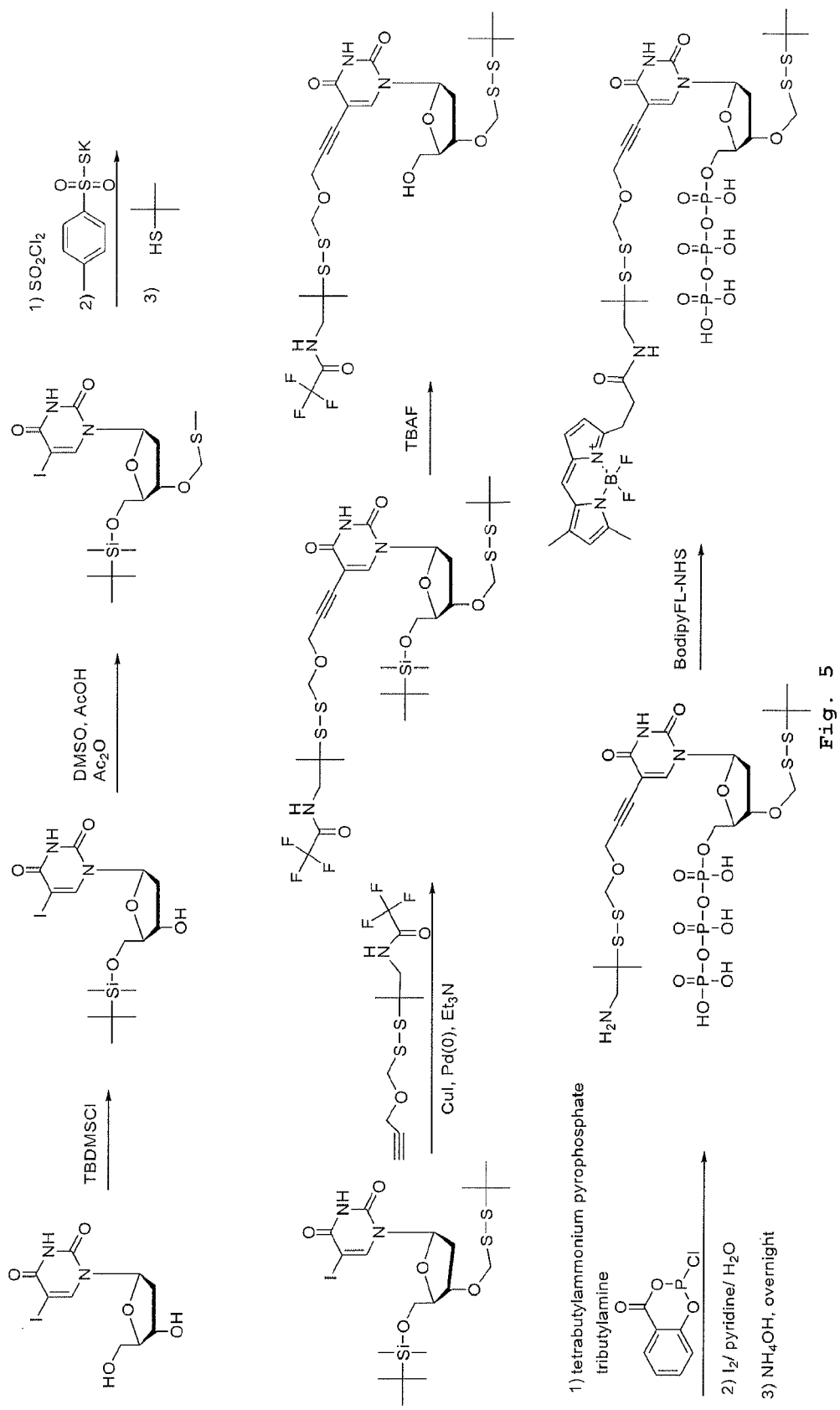
FIG. 5: Synthesis of 3'-O-SS(DTM)-dUTP-SS-BodipyFL.
Figure 6A:
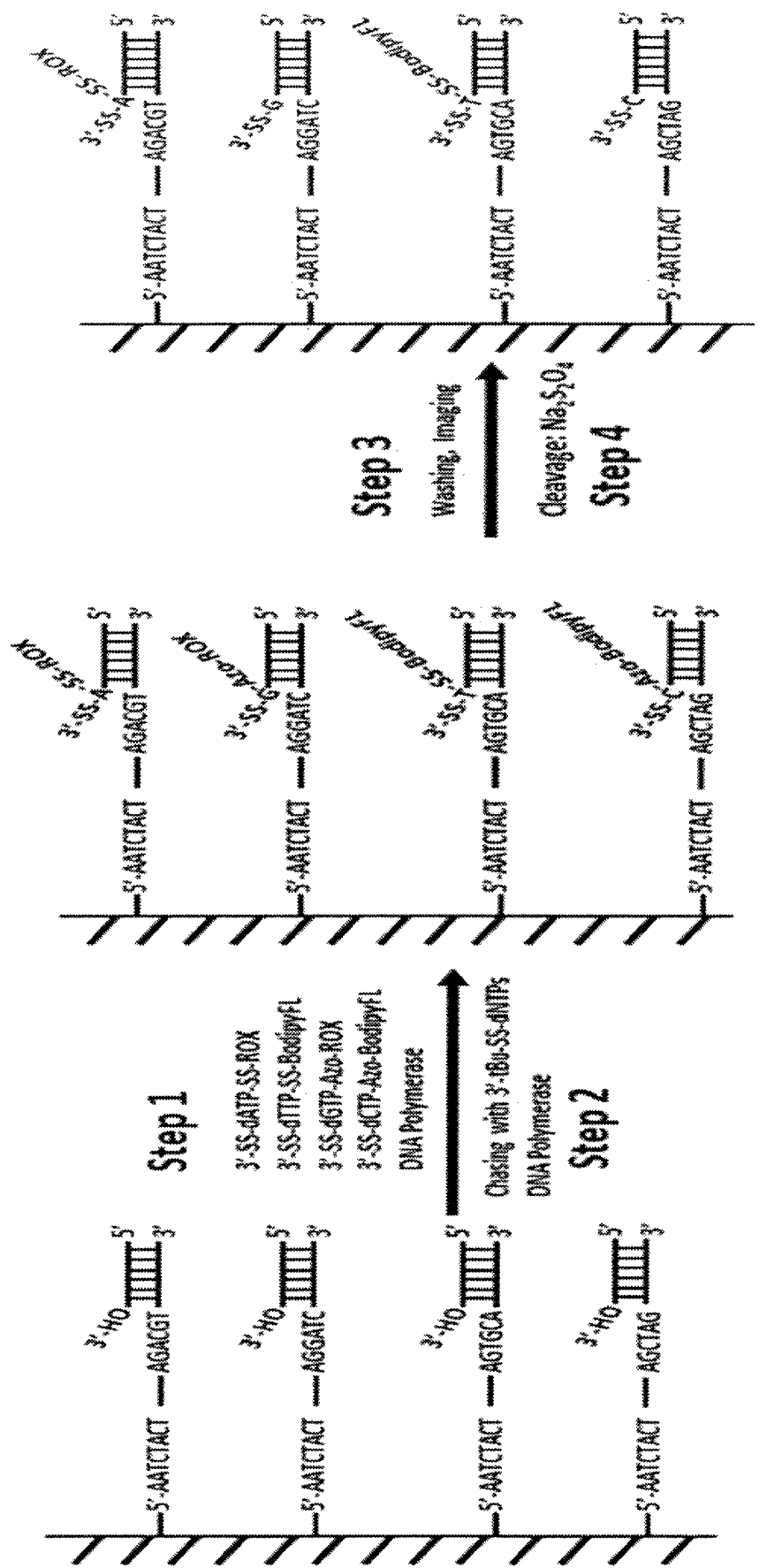
FIG. 6: Scheme 1: Use of 3'-O-SS(DTM)-dNTP-SS-Dyes (3'-O-SS-dATP-7-SS-Rox, 3'-O-SS-dTTP-5-SS-BodipyFL, 3'-O-SS-dGTP-7-Azo-Rox and 3'-O-SS-dCTP-5-Azo-BodipyFL) to perform 2-color DNA SBS. Step 1, Addition of DNA polymerase and the four nucleotide analogues (3'-O-SS-dATP-7-SS-Rox, 3'-O-SS-dTTP-5-SS-BodipyFL, 3'-O-SS-dGTP-7-Azo-Rox and 3'-O-SS-dCTP-5-Azo-BodipyFL) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye. Step 3, after washing away the unincorporated dye labeled nucleotides, detection of the unique fluorescence signal from each of the fluorescent dyes on the DNA products allows the identification of the incorporated nucleotide for sequence determination, Rox signal indicates incorporation of both A and G, BodipyFL signal indicates incorporation of T and C. Step 4, cleavage of Azo linker by adding sodium dithionite (Na$_2$S$_2$O$_4$) to the elongated DNA strands results in removal of Rox from incorporated G and BodipyFL from incorporated C. Step 5, after washing away the cleaved dyes, a second round of detection of the unique fluorescence signal from each of the fluorescent dyes on the DNA products allows the identification of the incorporated nucleotide for sequence determination. Disappearance of Rox signal indicates incorporation of G, and disappearance of BodipyFL signal indicates incorporation of C. Remaining Rox signal indicates incorporation of A, and remaining BodipyFL signal indicates incorporation of T. Next, in Step 6, treatment of the DNA products with THP cleaves the SS linker, leading to the removal of the remaining fluorescent dye and the regeneration of a free 3'-OH group on the DNA extension product, which is ready for the next cycle of the DNA sequencing reaction. The presence of an additional SS linkage between the Azo group and the base results in the production of a shorter scar on the incorporated nucleotide after THP treatment which should result in longer reads. Structures of modified nucleotides used in this scheme are shown in FIG. 1.
Figure 6B:
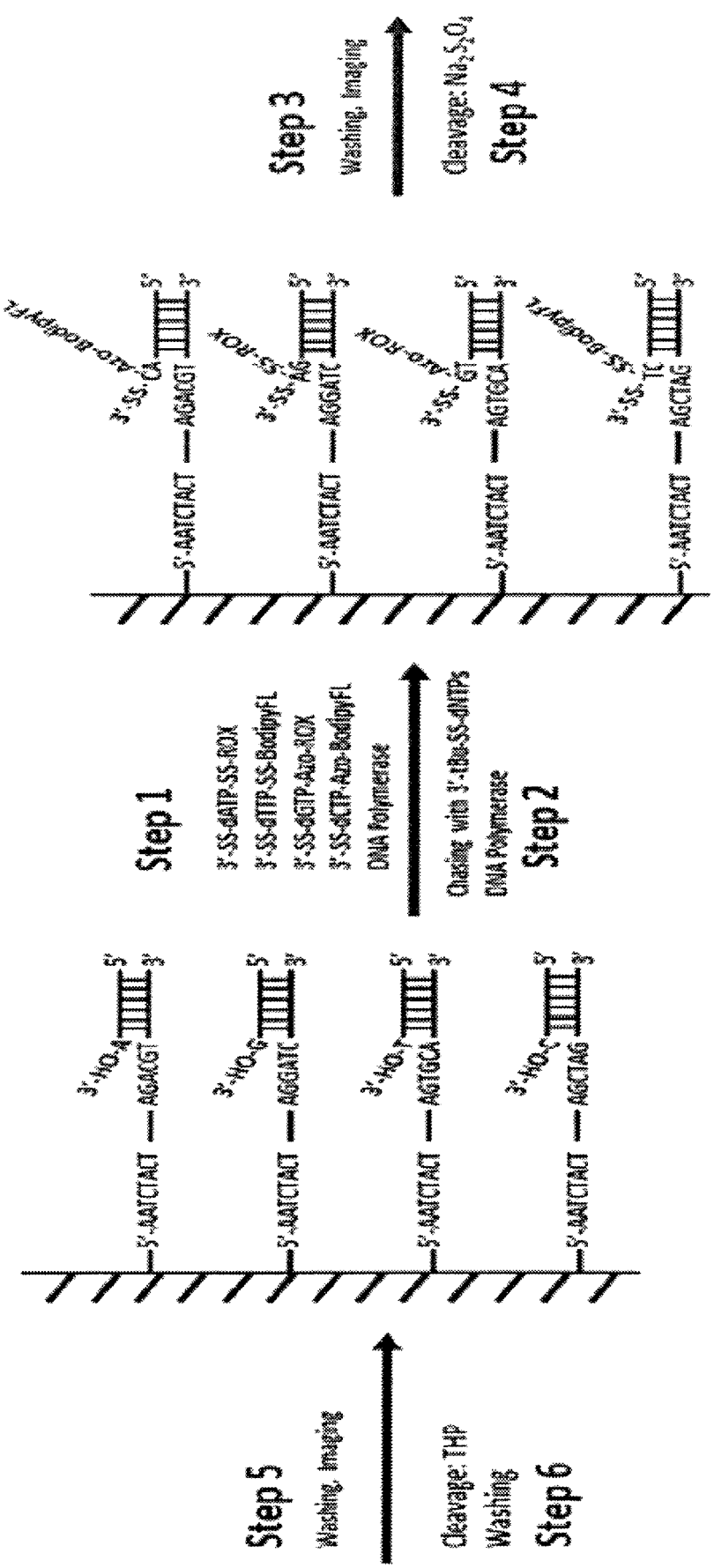
Figure 6C:
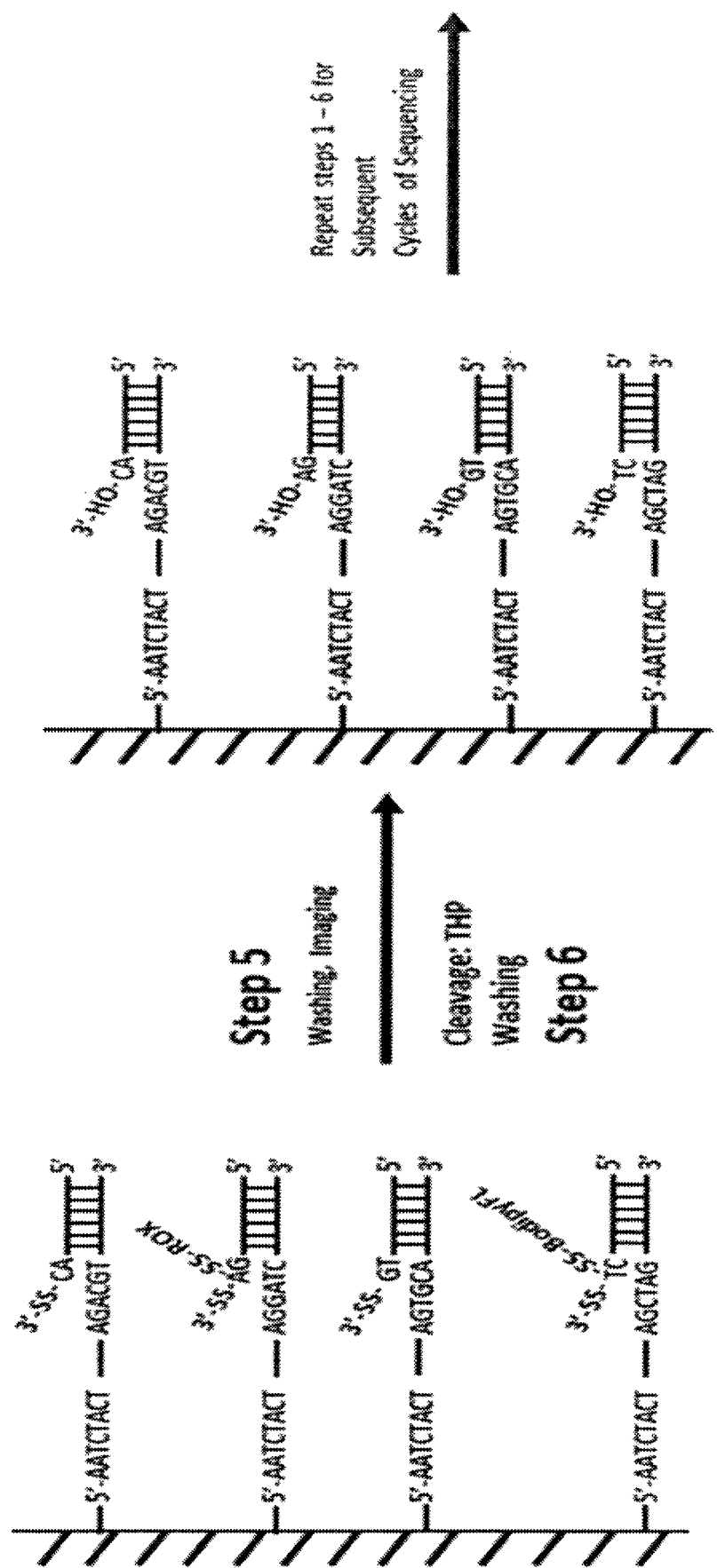

Step 5, after washing away the cleaved dyes, a second round of detection of the unique fluorescence signal from each of the fluorescent dyes on the DNA products allows the identification of the incorporated nucleotide for sequence determination. Disappearance of Rox signal indicates incorporation of G, and disappearance of BodipyFL signal indicates incorporation of C. Remaining Rox signal indicates incorporation of A, and remaining BodipyFL signal indicates incorporation of T. Next, in Step 6, treatment of the DNA products with THP cleaves the SS linker, leading to the removal of the remaining fluorescent dye and the regeneration of a free 3'-OH group on the DNA extension product, which is ready for the next cycle of the DNA sequencing reaction. The presence of an additional SS linkage between the Azo group and the base results in the production of a shorter scar on the incorporated nucleotide after THP treatment which should result in longer reads. Structures of modified nucleotides used in this scheme are shown in FIG. 1.

REFERENCES

1. Hyman E D (1988) A new method of sequencing DNA. Anal Biochem 174:423-436.
2. Ronaghi M, et al (1998) A sequencing method based on real-time pyrophosphate. Science 281:363-365.
3. Ju J, et al (2003) Massive Parallel Method for Decoding DNA and RNA, U.S. Pat. No. 6,664,079.
4. Li Z, Bai X, Ruparel H, Kim S, Turro N J, Ju J (2003) A photocleavable fluorescent nucleotide for DNA sequencing and analysis. Proc Natl Acad Sci USA 100:414-419.
5. Braslavsky I, et al (2003) Sequence information can be obtained from single DNA molecules. Proc Natl Acad Sci USA 100:3960-3964.
6. Ruparel H, et al (2005) Design and synthesis of a 3'-O-allyl photocleavable fluorescent nucleotide as a reversible terminator for DNA sequencing by synthesis. Proc Natl Acad Sci USA 102:5932-5937.
7. Margulies M, et al (2005) Genome sequencing in microfabricated high-density picolitre reactors. Nature 437:376-380.
8. Ju J, et al (2006) Four-color DNA sequencing by synthesis using cleavable fluorescent nucleotide reversible terminators. Proc Natl Acad Sci USA 103:19635-19640.
9. Wu J, et al (2007) 3'-O-modified nucleotides as reversible terminators for pyrosequencing. Proc Natl Acad Sci USA 104:16462-16467.
10. Guo J, et al (2008) Four-color DNA sequencing with 3'-O-modified nucleotide reversible terminators and chemically cleavable fluorescent dideoxynucleotides. Proc Natl Acad Sci USA 105:9145-9150.
11. Bentley D R, et al (2008) Accurate whole human genome sequencing using reversible terminator chemistry. Nature 456:53-59.
12. Harris T D, et al (2008) Single-molecule DNA sequencing of a viral genome. Science 320:106-109.
13. Eid, J, et al (2009) Real-time DNA sequencing from single polymerase molecules. Science 323:133-138.
14. Rothberg J M, et al (2011) An integrated semiconductor device enabling non-optical genome sequencing. Nature 475:348-352.
15. Turcatti G, Romieu A, Fedurco M, Tairi A P (2008) A new class of cleavable fluorescent nucleotides: synthesis and optimization as reversible terminators for DNA sequencing by synthesis. Nucleic Acids Res 36:e25.
16. Mitra R D, et al (2003) Fluorescent in situ sequencing on polymerase colonies. Anal Biochem 320:55-65.

What is claimed is:

1. A method for determining the nucleotide sequence of a single-stranded nucleic acid comprising:
   a) contacting the single-stranded nucleic acid with a primer, a nucleic acid polymerase and four types of tagged nucleotide analogues under conditions permitting the nucleic acid polymerase to catalyze incorporation of one of the tagged nucleotide analogues into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a nucleic acid extension product,
      wherein each type of the at least four types of tagged nucleotide analogues comprises: a base which is adenine, guanine, cytosine, thymine, or uracil, or a derivative of each thereof, a deoxyribose or ribose, and a cleavable blocking group bound to the 3'-oxygen of the deoxyribose or ribose that prevents the polymerase from catalyzing the incorporation of a subsequent nucleotide, and
      (i) the first type of nucleotide analogue comprises a first type of base and a first type of detectable label bound to the base via a first type of linker;
      (ii) the second type of nucleotide analogue comprises a second type of base and a second type of detectable label bound to the base via a second type of linker;
      (iii) the third type of nucleotide analogue comprises a third type of base and the first type of detectable label bound to the base via the second type of linker; and
      (iv) the fourth type of nucleotide analogue comprises fourth type of base and the second type of detectable label bound to the base via the first type of linker;
      wherein the first type and second type of linkers are different, and wherein the first type and second type of detectable label are different;
   b) identifying whether a nucleotide analogue comprising the first type or second type of detectable label was incorporated in step (a);
   c) contacting the incorporated tagged nucleotide analogue with a means of cleaving the first type of linker;
   d) determining whether the label was removed by the means of cleaving in step (c) so as to thereby determine the identity of the incorporated nucleotide analogue;
   e) contacting the incorporated tagged nucleotide analogue with a means of cleaving the second type of linker;
   f) cleaving the 3'-oxygen blocking group so as to thereby form a 3'-OH;
   g) iteratively performing steps (a)-(f) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product, so as to thereby determine the nucleotide sequence of the single-stranded nucleic acid.

2. A method for determining nucleotide sequence of a single-stranded nucleic acid comprising:
   a) contacting the single-stranded nucleic acid with a primer, a nucleic acid polymerase and a first type of tagged nucleotide analogue under conditions permitting the nucleic acid polymerase to catalyze incorporation of the tagged nucleotide analogue into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a DNA extension product,
   wherein the first type of tagged nucleotide analogue comprises a first type of base which is adenine, guanine, cytosine, thymine, or uracil, or a derivative of each thereof, a deoxyribose or ribose, a cleavable blocking group bound to the 3'-oxygen of the deoxyribose or ribose that prevents the polymerase from catalyzing the incorporation of a subsequent nucleotide, and a first type of detectable label bound to the base via a first type of linker,
   and if a tagged nucleotide is not incorporated, iteratively repeating the contacting with a second, third, and fourth type of tagged nucleotide analogue until a tagged nucleotide analogue is incorporated, wherein:
   (i) the second type of nucleotide analogue comprises a second type of base and a second type of detectable label bound to the base via a second type of linker;
   (ii) the third type of nucleotide analogue comprises a third type of base and the first type of detectable label bound to the base via the second type of linker; and
   (iii) the fourth type of nucleotide analogue comprises a fourth type of base and the second type of detectable label bound to the base via the first type of linker;
   wherein the first type and second type of linkers are different, and wherein the first type and second type of detectable label are different;
   b) identifying whether a nucleotide analogue comprising the first type or second type of detectable label was incorporated in step (a);
   c) contacting the incorporated nucleotide analogue with a means of cleaving the first type of linker;
   d) determining whether the detectable label was removed by the means of cleaving in step (c) so as to thereby determine the identity of the incorporated nucleotide analogue;
   e) contacting the incorporated tagged nucleotide analogue with a means of cleaving the second type of linker;
   f) cleaving the 3'-oxygen blocking group so as to thereby form a 3'-OH,
   g) iteratively performing steps (a)-(f) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product, so as to thereby determine the nucleotide sequence of the single-stranded nucleic acid.

3. The method of claim 1, wherein step (a) further comprising:
   contacting the single-stranded nucleic acid with four types of nucleotide reversible terminators, wherein each nucleotide reversible terminator comprises a blocking group to the 3'-oxygen of the deoxyribose or ribose that prevents the polymerase from catalyzing incorporation of a subsequent nucleotide, under conditions permitting the nucleic acid polymerase to catalyze incorporation of one of the nucleotide reversible terminators into the primer if:
   (i) the polymerase failed to incorporate a tagged nucleotide analogue in step a), and
   (ii) the nucleotide reversible terminator is complementary to the nucleotide residue of the single-stranded nucleic acid which is immediately 5' to a nucleotide residue of the single-stranded nucleic acid hybridized to the 3' terminal nucleotide residue of the primer.

4. The method of claim 2, wherein step (a) further comprising:
   contacting the single-stranded nucleic acid with four types of nucleotide reversible terminators wherein each nucleotide reversible terminator comprises a blocking group to the 3'-oxygen of the deoxyribose or ribose that prevents the polymerase from catalyzing incorporation of a subsequent nucleotide, under conditions permitting the nucleic acid polymerase to catalyze incorporation of one of the nucleotide reversible terminators into the primer if:
   (i) the polymerase failed to incorporate a tagged nucleotide analogue in step a), and
   (ii) the nucleotide reversible terminator is complementary to the nucleotide residue of the single-stranded nucleic acid which is immediately 5' to a nucleotide residue of the single-stranded nucleic acid hybridized to the 3' terminal nucleotide residue of the primer.

5. The method of claim 4, wherein
   the 3'-oxygen blocking group of the nucleotide reversible terminators is bound to the 3'-oxygen by at least one orthogonal chemically cleavable linker.

6. The method of claim 1, wherein: (A) the first base is A, or derivative thereof and:
   (i) the second base is T/U or a derivative thereof, the third base is C or a derivative thereof, and the fourth base is G or a derivative thereof,
   (ii) the second base is T/U or a derivative thereof, the third base is G or a derivative thereof, and the fourth base is C or a derivative thereof,
   (iii) the second base is C or a derivative thereof, the third base is T/U or a derivative thereof, and the fourth base is G or a derivative thereof,
   (iv) the second base is C or a derivative thereof, the third base is G or a derivative thereof, and the fourth base is T/U or a derivative thereof,
   (v) the second base is G or a derivative thereof, the third base is T/U or a derivative thereof, and the fourth base is C or a derivative thereof, or (vi) the second base is G or a derivative thereof, the third base is C or a derivative thereof, and the fourth base is T/U or a derivative thereof;

(B) the first base is T/U, or derivative thereof and:
(i) the second base is C or a derivative thereof, the third base is A or a derivative thereof, and the fourth base is G or a derivative thereof,
(ii) the second base is C or a derivative thereof, the third base is G or a derivative thereof, and the fourth base is A or a derivative thereof,
(iii) the second base is A or a derivative thereof, the third base is C or a derivative thereof, and the fourth base is G or a derivative thereof,
(iv) the second base is A or a derivative thereof, the third base is G or a derivative thereof, and the fourth base is C or a derivative thereof,
(v) the second base is G or a derivative thereof, the third base is C or a derivative thereof, and the fourth base is A or a derivative thereof, or
(vi) the second base is G or a derivative thereof, the third base is A or a derivative thereof, and the fourth base is C or a derivative thereof;

(C) the first base is C, or derivative thereof and:
(i) the second base is A or a derivative thereof, the third base is T/U or a derivative thereof, and the fourth base is G or a derivative thereof,
(ii) the second base is A or a derivative thereof, the third base is G or a derivative thereof, and the fourth base is T/U or a derivative thereof,
(iii) the second base is T/U or a derivative thereof, the third base is A or a derivative thereof, and the fourth base is G or a derivative thereof,
(iv) the second base is T/U or a derivative thereof, the third base is G or a derivative thereof, and the fourth base is A or a derivative thereof,
(v) the second base is G or a derivative thereof, the third base is T/U or a derivative thereof, and the fourth base is A or a derivative thereof, or
(vi) the second base is G or a derivative thereof, the third base is A or a derivative thereof, and the fourth base is T/U or a derivative thereof; or (D) the first base is G, or derivative thereof and:
(i) the second base is C or a derivative thereof, the third base is T/U or a derivative thereof, and the fourth base is A or a derivative thereof,
(ii) the second base is C or a derivative thereof, the third base is A or a derivative thereof, and the fourth base is T/U or a derivative thereof,
(iii) the second base is T/U or a derivative thereof, the third base is A or a derivative thereof, and the fourth base is C or a derivative thereof,
(iv) the second base is T/U or a derivative thereof, the third base is C or a derivative thereof, and the fourth base is A or a derivative thereof,
(v) the second base is A or a derivative thereof, the third base is T/U or a derivative thereof, and the fourth base is C or a derivative thereof, or
the second base is A or a derivative thereof, the third base is C or a derivative thereof, and the fourth base is T/U or a derivative thereof.

7. The method of claim 1, wherein the first type of linker and/or second type of linker comprises orthogonal chemically cleavable linkers.

8. The method of claim 1, wherein the tagged nucleotide analogues are selected from the group comprising:

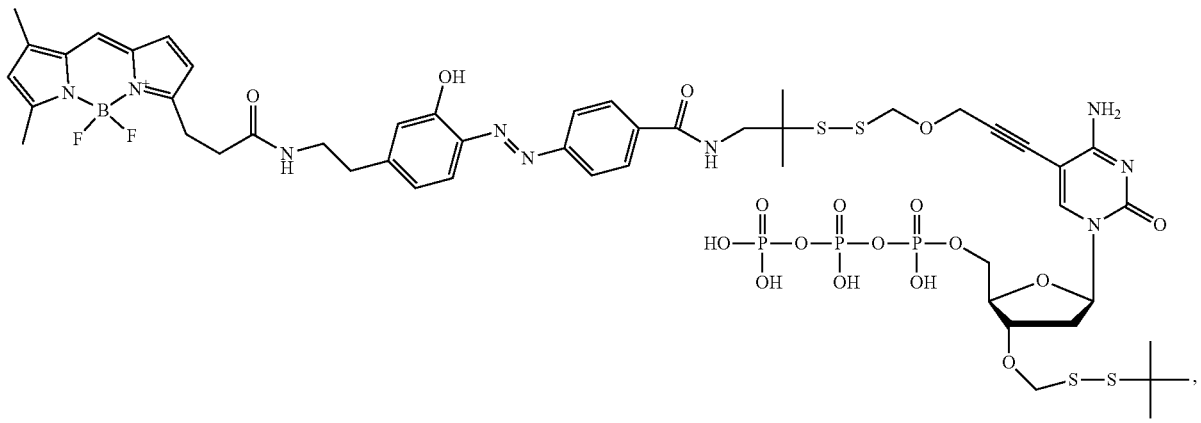

-continued
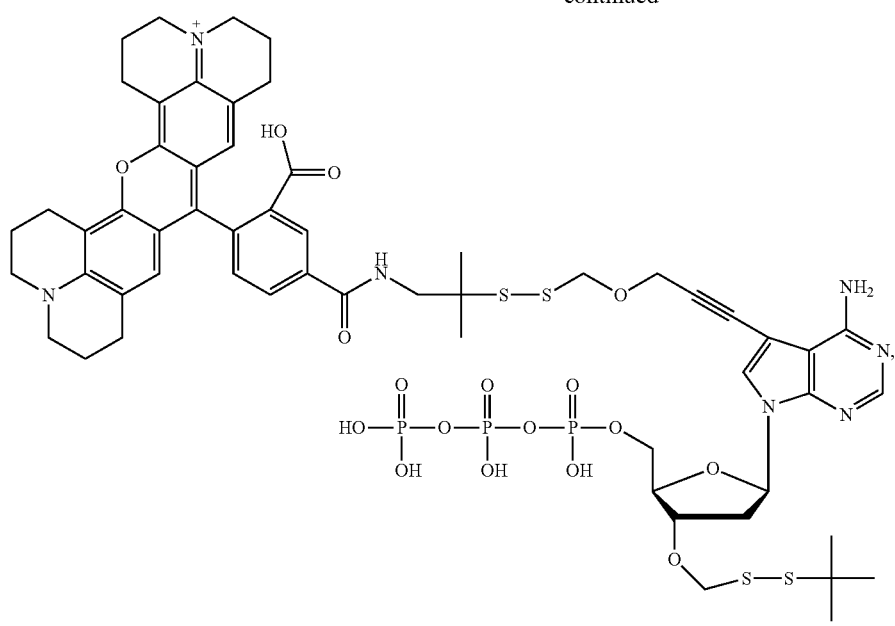
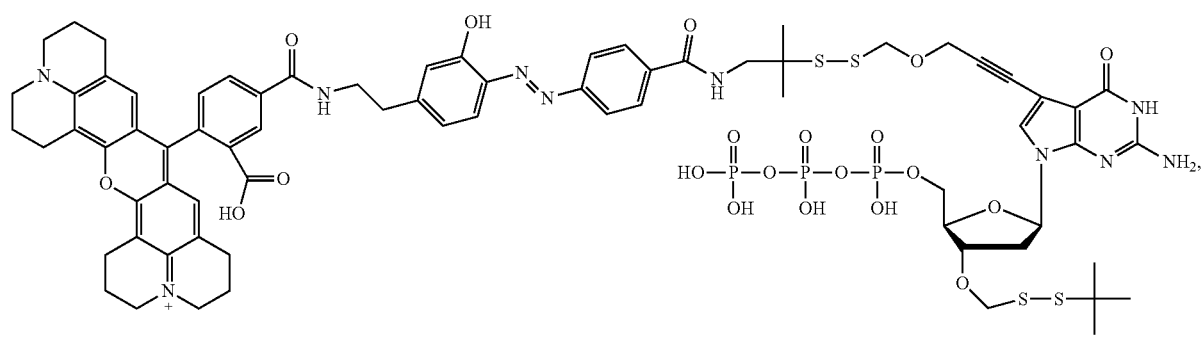
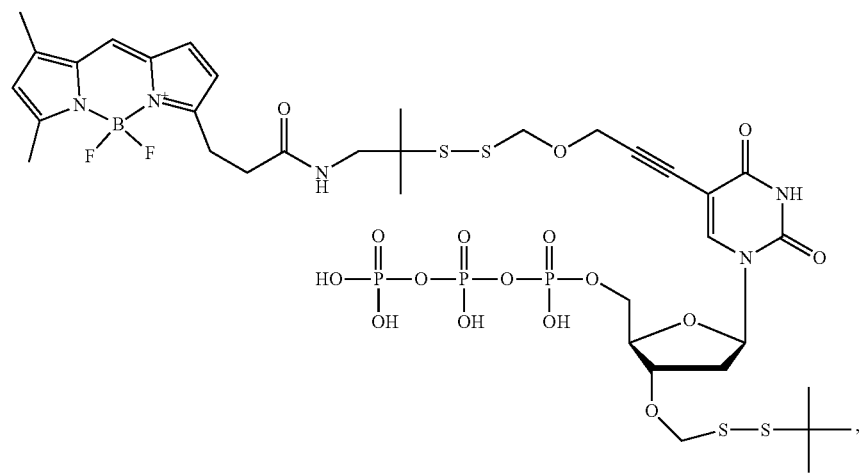

-continued

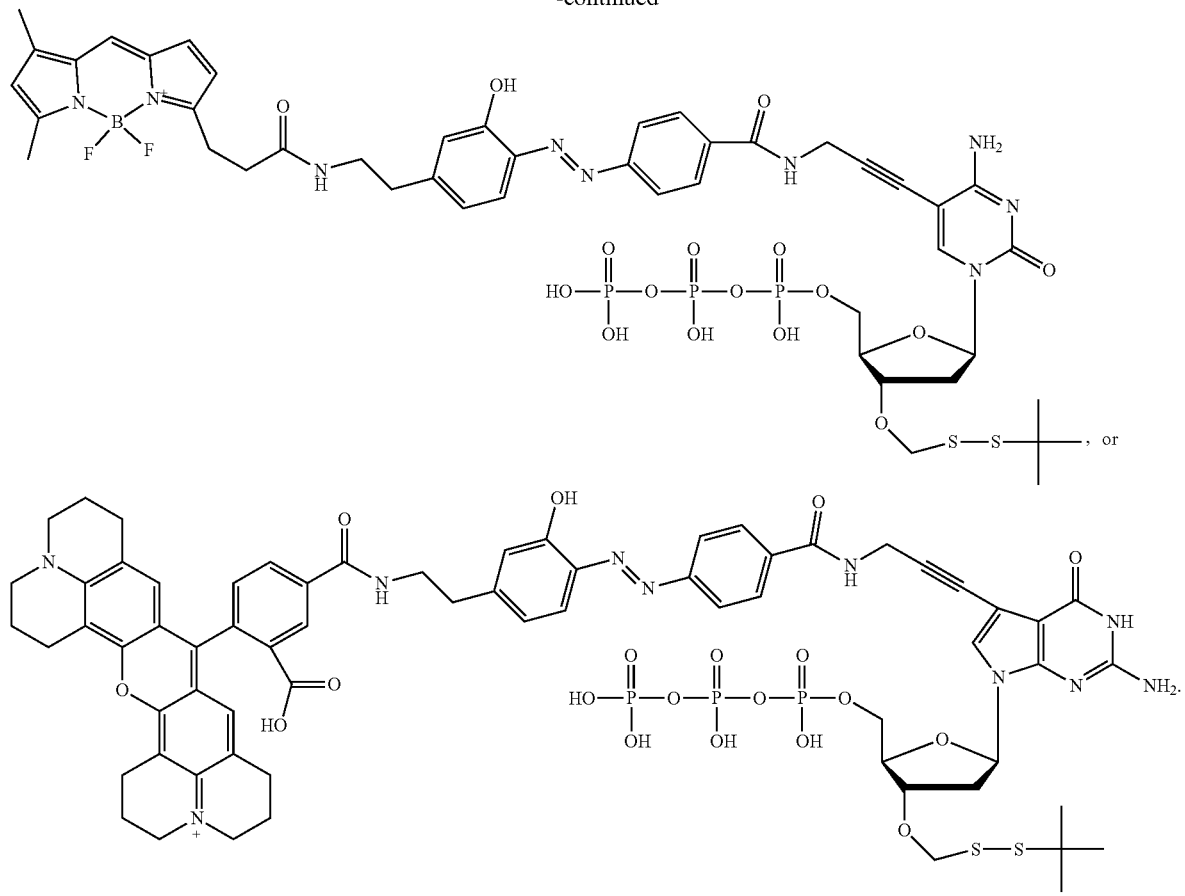

9. The method of claim 4, wherein the blocking group of the nucleotide reversible terminators comprises an alkyldithiomethyl, or wherein the blocking group of the nucleotide reversible terminators and/or first and/or second type of linker is chemically cleaved or photocleaved.

10. The method of claim 9, wherein the blocking group of the nucleotide reversible terminators and/or first and/or second type of linker is cleaved by a water soluble phosphine, thereby resulting in a 3'-OH.

11. The method of claim 10, wherein the water soluble phosphine is tris-(2-carboxyethyl)phosphine (TCEP) or tris(hydroxypropyl)phosphine (THP).

12. The method of claim 4, wherein the nucleotide reversible terminators are 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP.

13. The method of claim 4, wherein the 3'-oxygen blocking group of the tagged nucleotide analogues is bound to the 3'-oxygen by at least one orthogonal chemically cleavable linker, or wherein the blocking group of the tagged nucleotide analogues comprises a dithiomethyl, azidomethyl, azo, allyl, and/or 2-nitrobenzl.

14. The method of claim 4, wherein the blocking group of the tagged nucleotide analogues comprises an alkyldithiomethyl; or wherein the base of one or more of the first, second, third, and/or fourth type of nucleotide analogue comprise a deazapurine base.

15. The method of claim 1, wherein the first type of linker and/or second type of linker comprises orthogonal chemically cleavable linkers.

16. The method of claim 1, wherein the first and/or second type of linkers comprise one or more of an alkyldithiomethyl linker, an azo linker, an allyl linker, a nitrobenzyl linker, an azidomethyl linker, and/or a dimethyl ketal linker.

17. The method of claim 1, wherein the first and/or second type of detectable label is one or more of a dye, a fluorophore, a fluorescence energy transfer tag, a chemiluminescent compound, a chromophore, a mass tag, an electrophore, a mononucleotide, an oligonucleotide, or a combination thereof.

18. The method of claim 1, wherein the first and/or second B type of detectable label is a fluorophore.

19. The method of claim 1, wherein the first and/or second type of detectable label is BodipyFL, R6G, ROX, Cy5, or Alexa488; viii) the nucleotide comprises one or more of 3'-O-SS-dATP-7-SS-Rox, 3'-O-SS-dTTP-5-SS-BodipyFL, 3'-O-SS-dGTP-7-Azo-Rox or 3'-O-SS-dCTP-5-Azo-BodipyFL; ix) the first type of linker is an alkyldithiomethyl linker and the second type of linker is an azo linker.

20. The method of claim 4, wherein the blocking group of the nucleotide reversible terminators and/or the first and/or second type of linkers is cleaved by sodium dithionite.

* * * * *